US012154201B2

(12) United States Patent
Pollard et al.

(10) Patent No.: US 12,154,201 B2
(45) Date of Patent: Nov. 26, 2024

(54) SYSTEMS AND METHODS FOR MODIFYING A SAFETY BOUNDARY FOR VIRTUAL REALITY SYSTEMS

(71) Applicant: Meta Platforms Technologies, LLC, Menlo Park, CA (US)

(72) Inventors: John Pollard, Fairview, TX (US); Jimmy K. Yun, Mountain View, CA (US); Jason Dong Uk Kim, Lucas, TX (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 18/362,260

(22) Filed: Jul. 31, 2023

(65) Prior Publication Data

US 2023/0377744 A1 Nov. 23, 2023

Related U.S. Application Data

(63) Continuation of application No. 17/665,211, filed on Feb. 4, 2022, now Pat. No. 11,741,649, which is a
(Continued)

(51) Int. Cl.
*G06T 11/60* (2006.01)
*G06F 3/01* (2006.01)
(Continued)

(52) U.S. Cl.
CPC ............. *G06T 11/60* (2013.01); *G06F 3/011* (2013.01); *G06T 5/80* (2024.01); *G06T 11/001* (2013.01); *G16H 40/67* (2018.01)

(58) Field of Classification Search
CPC ............ G06T 11/60; G06T 5/80; G16H 40/67
(Continued)

(56) References Cited

U.S. PATENT DOCUMENTS 8,896,629 B2 11/2014 Meier et al.
9,754,167 B1 9/2017 Holz et al.
(Continued)

FOREIGN PATENT DOCUMENTS

CN 102473324 A 5/2012
CN 107408146 A 11/2017
(Continued)

OTHER PUBLICATIONS

Co-Pending U.S. Appl. No. 15/981,132, filed May 16, 2018, 56 Pages.
(Continued)

*Primary Examiner* — Thomas J Lett
(74) *Attorney, Agent, or Firm* — Greenberg Traurig, LLP

(57) ABSTRACT

The disclosed computer-implemented method may include establishing a virtual boundary for a virtual-world environment in reference to a real-world environment, and determining whether the virtual boundary requires a correction. The method may include providing, in response to determining that the virtual boundary requires the correction, and alert and, in response to the alert, receiving a request from a user to modify the virtual boundary. The method may further include monitoring, in response to the request from the user, an orientation of a direction indicator to generate orientation data, and modifying the virtual boundary based on the orientation data. Various other methods, systems, and computer-readable media are also disclosed.

33 Claims, 14 Drawing Sheets

Related U.S. Application Data continuation of application No. 16/177,424, filed on Oct. 31, 2018, now Pat. No. 11,244,483.

(51) Int. Cl.
  *G06T 5/80* (2024.01)
  *G06T 11/00* (2006.01)
  *G16H 40/67* (2018.01)

(58) Field of Classification Search
  USPC .......................................................... 705/2
  See application file for complete search history.

(56) References Cited

U.S. PATENT DOCUMENTS

| | | | |
|---|---|---|---|
| 9,965,471 | B2 | 5/2018 | Huston et al. |
| 9,971,854 | B1 | 5/2018 | Bowen |
| 2007/0173265 | A1 | 7/2007 | Gum |
| 2009/0307608 | A1 | 12/2009 | Kalasapur et al. |
| 2012/0176410 | A1 | 7/2012 | Meier et al. |
| 2016/0124052 | A1 | 5/2016 | Inguva et al. |
| 2016/0124502 | A1 | 5/2016 | Sawyer et al. |
| 2016/0270648 | A1 | 9/2016 | Freeman et al. |
| 2017/0103574 | A1 | 4/2017 | Faaborg et al. |
| 2017/0364159 | A1 | 12/2017 | Eronen et al. |
| 2018/0012370 | A1 | 1/2018 | Aghamohammadi et al. |
| 2019/0043259 | A1* | 2/2019 | Wang ..................... G06F 3/012 |
| 2019/0295285 | A1 | 9/2019 | Shinohara |
| 2021/0333798 | A1 | 10/2021 | Kato |

FOREIGN PATENT DOCUMENTS

| | | |
|---|---|---|
| CN | 107430439 A | 12/2017 |
| CN | 107850943 A | 3/2018 |
| JP | 2017055173 A | 3/2017 |
| JP | 2017535901 A | 11/2017 |
| JP | 2018508851 A | 3/2018 |
| KR | 20170081225 A | 7/2017 |
| WO | 2016102768 A1 | 6/2016 |
| WO | 2018158896 A1 | 9/2018 |

OTHER PUBLICATIONS

European Search Report for European Patent Application No. 23169413.4, dated Jul. 6, 2023, 4 pages.

Extended European Search Report for European Application No. 18938341.7, mailed Nov. 12, 2021, 9 Pages.

Gepp M., "Roomscale 101—An Introduction to Roomscale VR," Blog at Vive.com [online], Oct. 25, 2017, 3 pages, Retrieved from the Internet: URL: https://blog.vive.com/US/2017/10/25/roomscale-101/.

Highfield V., "HTC Vive Ups Resolution to 3K with HTC Vive Pro Headset at CES2018," Posted on Jan. 9, 2018, 5 pages, Retrieved from the Internet: URL: https://www.pcauthority.com.au/news/htc-vive-ups-resolution-to-3k-with-htc-vive-pro-headset-at-ces-2018-480750.

Holly R., "Lenovo Mirage Solo Hands-On: The First Daydream Headset that doesn't Need a Phone," May 29, 2018, 12 pages, Retrieved from the Internet: URL: https://www.androidcentral.com/lenovo-mirage-solo.

International Search Report and Written Opinion for International Application No. PCT/US2018/066974, mailed Jul. 31, 2019, 13 Pages.

Lai R., "I Can Finally Do Cartwheels in VR with HTC's Vive Focus," Posted on Engadget.com [online], Posted Date: Dec. 13, 2017, 16 pages, Retrieved from the Internet: URL: https://www.engadget.com/2017-12-13-htc-vive-focus- cartwheel-video-hands-on.html.

Lang B., "Hands-on: Lenovo Mirage Solo-Strong Fundamentals, Questionable Pricing," Posted on Roadtovr.com [online], Posted Date: Jan. 17, 2018, 5 pages, Retrieved from the Internet: URL: https://www.roadtovr.com/ces-2018-lenovo-mirage-solo-hands-on-strong-fundamentals-questionable-pricing/.

Office Action mailed Apr. 11, 2023 for Japanese Patent Application No. 2021-548502, filed on Dec. 20, 2018, 5 pages.

Office Action mailed Oct. 11, 2023 for Korean Application No. 10-2021-7016331, filed Dec. 20, 2018, 8 pages.

Office Action mailed Jan. 25, 2024 for Chinese Application No. 201880100579.5, filed Dec. 20, 2018, 15 pages.

Office Action mailed Sep. 6, 2022 for Japanese Patent Application No. 2021-548502, filed on Dec. 20, 2018, 6 pages.

Shanklin W., "Lenovo's VR Headset Is Cheaper and More Comfortable Than Rift and Vive," Jan. 5, 2017 [Retrieved on May 29, 2018], 17 pages, Retrieved from the Internet: URL: https://newatlas.com/lenovo-vr-headset-review-hands-on-2017/47245/.

Office Action mailed Jun. 7, 2024 for Korean Application No. 10-2021-7016331, filed Dec. 20, 2018, 7 pages.

Office Action mailed Aug. 6, 2024 for Japanese Patent Application No. 2023-078135, filed on May 10, 2023, 3 pages.

\* cited by examiner

SYSTEMS AND METHODS FOR MODIFYING A SAFETY BOUNDARY FOR VIRTUAL REALITY SYSTEMS

CROSS REFERENCE TO RELATED APPLICATION

This application is a continuation of U.S. application Ser. No. 17/665,211, filed 4 Feb. 2022, which is a continuation of U.S. application Ser. No. 16/177,424, filed 31 Oct. 2018, now U.S. Pat. No. 11,244,483, the disclosures of each of which are incorporated, in their entirety, by this reference.

BACKGROUND

Virtual reality (VR) systems and augmented reality (AR) systems may enable users to have more immersive experiences than ordinary television or video gaming can provide. While wearing a head-mounted display (HMD), a user can view different portions of a captured scene or an artificially generated scene simply by orienting his or her head, just as the user naturally does to view a real-world environment. The scene may be presented in the HMD to the user based on the position and orientation of the user's head, such that the scene changes based on changes in the position and orientation of the user's head. A mobile VR system can also account for the movement of the user as the user walks around in the real-world environment, such that the user perceives him or herself to be moving in a virtual environment.

Although immersive, these features may permit the user to engage with the virtual environment in a way that causes the user to forget important aspects of the user's real-world environment. For example, a user trying to walk from one position in a virtual environment to another position may fail to account for (or be unable to see) a real-world obstacle, such as a table, a couch, or a wall due to the user's lack of awareness of the real-world environment. This may result in a collision with the real-world environment or a feature in the real-world environment.

SUMMARY

As will be described in greater detail below, the instant disclosure describes systems and methods that may enable a user who is wearing an HMD device to modify a virtual boundary in a real-world environment that can be used to prevent collisions with features or obstacles in the real-world environment.

In one example, a computer-implemented method for modifying a virtual boundary may include (1) establishing a virtual boundary for a virtual-world environment in reference to a real-world environment, (2) determining whether the virtual boundary requires a correction, (3) in response to determining that the virtual boundary requires the correction, providing an alert, (4) in response to the alert, receiving a request from a user to modify the virtual boundary, (5) in response to the request from the user, monitoring an orientation of a direction indicator to generate orientation data, and (6) modifying the virtual boundary based on the orientation data.

In some examples, determining whether the virtual boundary requires a correction may include checking the virtual boundary for an error. In some examples, the error may include at least one of an unclosed loop, a zero-area portion, or a portion that does not satisfy a minimum portion area threshold. In some examples, the method may include automatically correcting the error. In some examples, the alert may be a visual or audible notification.

In some examples, the method may further include (a) capturing a view of the real-world environment with an imaging system of a head-mounted display system, the captured view having lens-induced distortion, (b) correcting the lens-induced distortion in the captured view to produce a compensated view of the real-world environment, (c) superimposing the virtual boundary on the compensated view of the real-world environment, and (d) displaying the compensated view of the real-world environment in a display of the head-mounted display system. In some examples, providing the alert may include displaying the virtual boundary in a warning color when the virtual boundary requires a correction. In some examples, the virtual boundary may be displayed as a filled-in shape defined by the virtual boundary.

In some examples, the orientation data may include elevation data of an elevation of the direction indicator with respect to a reference elevation representing a plane of the real-world environment. In some examples, modifying the virtual boundary may include determining an intersection between the plane and a virtual line that extends from the direction indicator at an elevation indicated by the elevation data and at the orientation indicated by the orientation data. In some examples, modifying the virtual boundary may include adding portions to or subtracting portions from the virtual boundary.

In some examples, the above-described method may be encoded as computer-readable instructions on a computer-readable medium. For example, a computer-readable medium may include one or more computer-executable instructions that, when executed by at least one processor of a computing device, may cause the computing device to (1) establish a virtual boundary for a virtual-world environment in reference to a real-world environment, (2) determine whether the virtual boundary requires a correction, (3) in response to determining that the virtual boundary requires the correction, provide an alert, (4) in response to the alert, receive a request from a user to modify the virtual boundary, (5) in response to the request from the user, monitor an orientation of a direction indicator to generate orientation data, and (6) modify the virtual boundary based on the orientation data.

In some examples, determining whether the virtual boundary requires a correction may include checking the virtual boundary for an error. In some examples, the error may include at least one of an unclosed loop, a zero-area portion, or a portion that does not satisfy a minimum portion area threshold. In some examples, the processor may be configured to automatically correct the error.

In some examples, the processor may be further configured to: (a) capture a view of the real-world environment with an imaging system of a head-mounted display system, the captured view having lens-induced distortion, (b) correct the lens-induced distortion in the captured view to produce a compensated view of the real-world environment, (c) superimpose the virtual boundary on the compensated view of the real-world environment, and (d) display the compensated view of the real-world environment in a display of the head-mounted display system. In some examples, providing the alert may include displaying the virtual boundary in a warning color when the virtual boundary requires a correction.

In some examples, the orientation data may include elevation data of an elevation of the direction indicator with respect to a reference elevation representing a plane of the real-world environment. In some examples, modifying the virtual boundary may include determining an intersection between the plane and a virtual line that extends from the direction indicator at an elevation indicated by the elevation data and at the orientation indicated by the orientation data.

In addition, a head-mounted display system may include a display secured to a user attachment system, a direction indicator, and a processing system. The processing system may be configured to (1) determine whether a virtual boundary for a virtual-world environment in reference to a real-world environment requires a correction, (2) in response to determining that the virtual boundary requires the correction, provide an alert, (3) in response to the alert, receive a request from a user to modify the virtual boundary, (4) in response to the request from the user, monitor an orientation of a direction indicator to generate orientation data, and (5) modify the virtual boundary based on the orientation data.

In some examples, determining whether the virtual boundary requires a correction may include checking the virtual boundary for an error. In some examples, the error may include at least one of an unclosed loop, a zero-area portion, or a portion that does not satisfy a minimum portion area threshold. In some examples, the processing system may be further configured to automatically correct the error.

In some examples, the head-mounted display system may further include an imaging system. In some examples, the processing system may be further configured to: (a) capture a view of the real-world environment with the imaging system, the captured view having lens-induced distortion, (b) correct the lens-induced distortion in the captured view to produce a compensated view of the real-world environment, (c) superimpose the virtual boundary on the compensated view of the real-world environment, and (d) display the compensated view of the real-world environment in the display. In some examples, providing the alert may include displaying the virtual boundary in a warning color when the virtual boundary requires a correction.

In some examples, the orientation data may include elevation data of an elevation of the direction indicator with respect to a reference elevation representing a plane of the real-world environment. In some examples, modifying the virtual boundary may include determining an intersection between the plane and a virtual line that extends from the direction indicator at an elevation indicated by the elevation data and at the orientation indicated by the orientation data.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
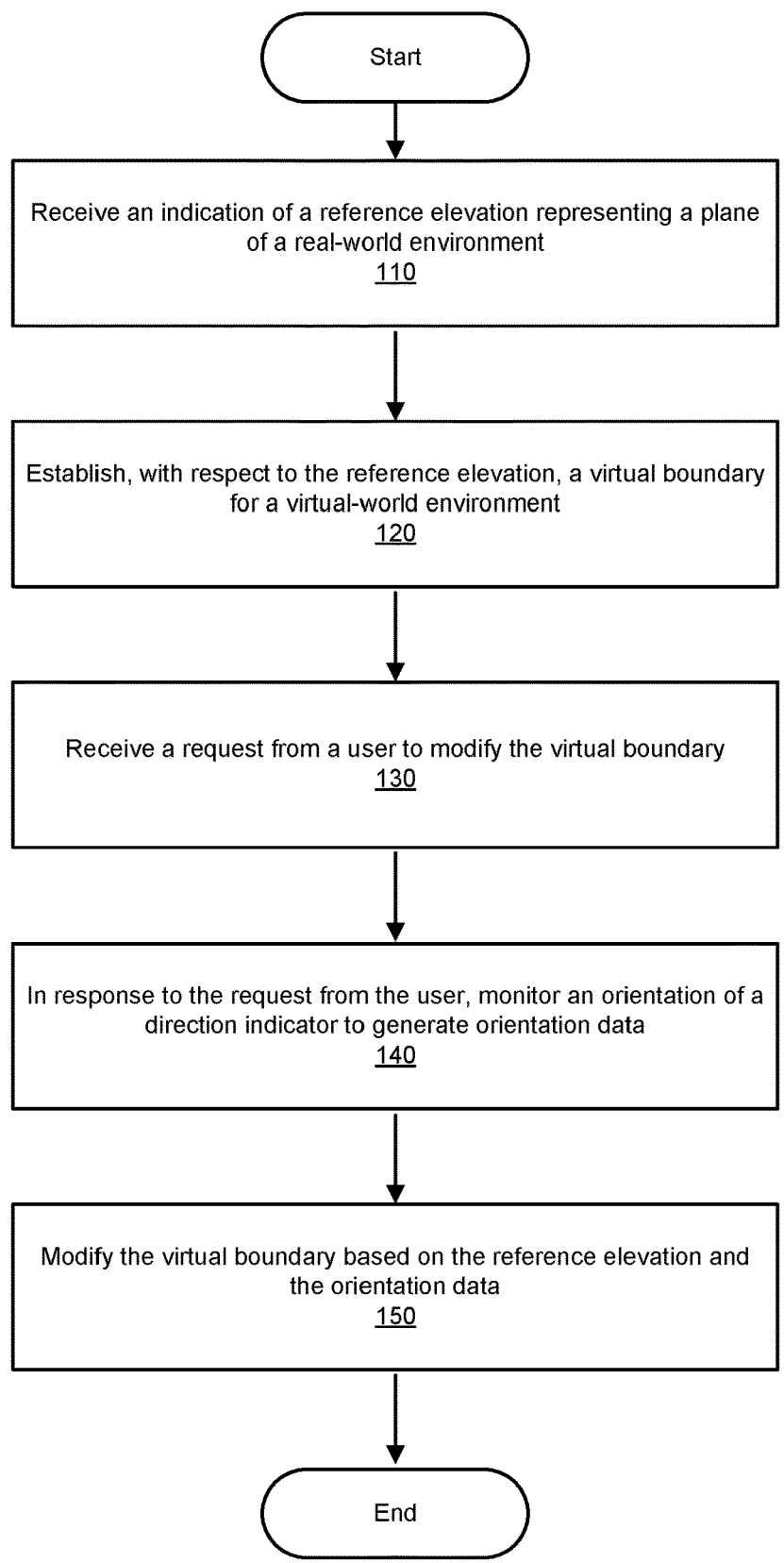
FIG. 1 is a flow diagram of an exemplary method for modifying a virtual boundary relative to a real-world environment, according to aspects of the present disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to systems and methods that allow a user to modify a virtual boundary relative to the user's real-world environment and/or a virtual environment. As will be explained in greater detail below, embodiments of the instant disclosure may allow the user to modify a virtual boundary on the floor of the real-world environment by using, for example, a hand-held controller, a finger, an eye-gaze, or other direction indicator. The user may "draw" (e.g., draw virtually using a direction indicator) modifications to the virtual boundary. While the user is wearing the HMD device, a view of the real-world environment may be provided by one or more cameras disposed on the HMD device. These cameras may permit a pass-through view that shows the real-world environment as if the user were not wearing the HMD device. In this way, the user may see features of the environment and obstacles to be avoided and may define and modify the virtual boundary a safe distance away from such features.

In some embodiments, the user may use a direction indicator to point to a location on the floor of the real-world environment. For example, an HMD system may include a hand-held controller that can be used to point to the floor. Position and orientation information of the hand-held controller may be used by a processing subsystem to identify a specific point on the floor, such as by using a height of the hand-held controller over the floor and the orientation of the hand-held controller. During a boundary modification state, the virtual boundary may be displayed on the floor, and a virtual line may appear to the user to extend from the hand-held controller toward the floor to provide visual feedback to the user while the user modifies the virtual boundary on the floor.

After modifying the virtual boundary, an indication of the virtual boundary and/or a boundary wall derived from the virtual boundary may be presented to the user in the HMD device whenever the user comes within a threshold distance of the virtual boundary to make the user aware of the real-world environment and/or to prevent the user from tripping, falling, or knocking an object over. Relying on the virtual boundary, the user can keep the HMD device on and safely move about the real-world environment in order to better engage with a virtual environment presented to the user during an operational state. The aspects described herein may improve VR and AR technology by providing a safety feature without requiring additional sensors or specialized hardware. In addition, the aspects described herein may improve the functioning of a computer by providing a safety feature that may be implemented without requiring additional resources. For example, the safety feature may be implemented without requiring substantial processing and memory resources from the computer and therefore may not negatively affect computing performance.

Figure 2:
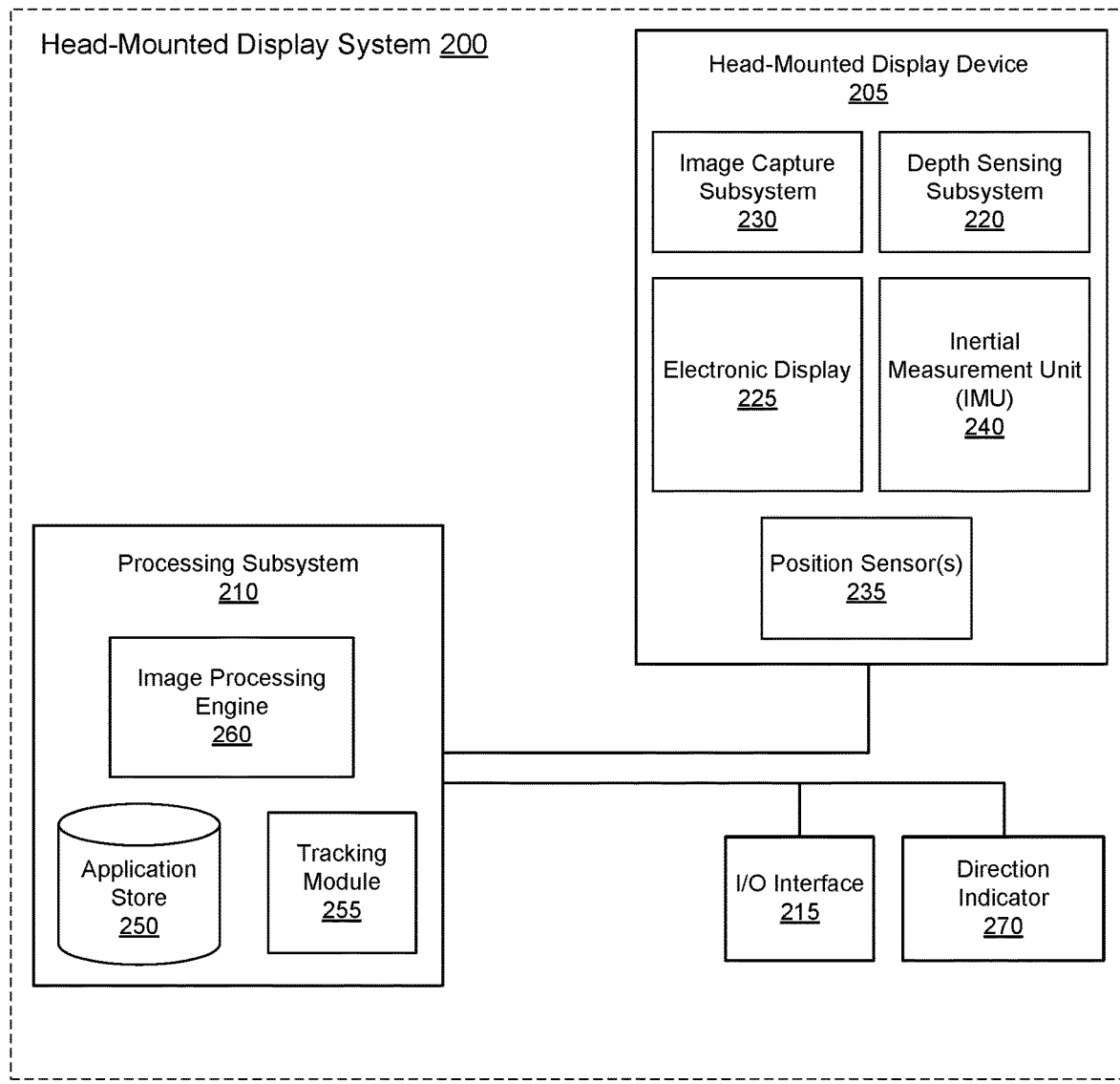
FIG. 2 is a block diagram of an exemplary head-mounted display (HMD) system, according to aspects of the present disclosure.
Figure 3:
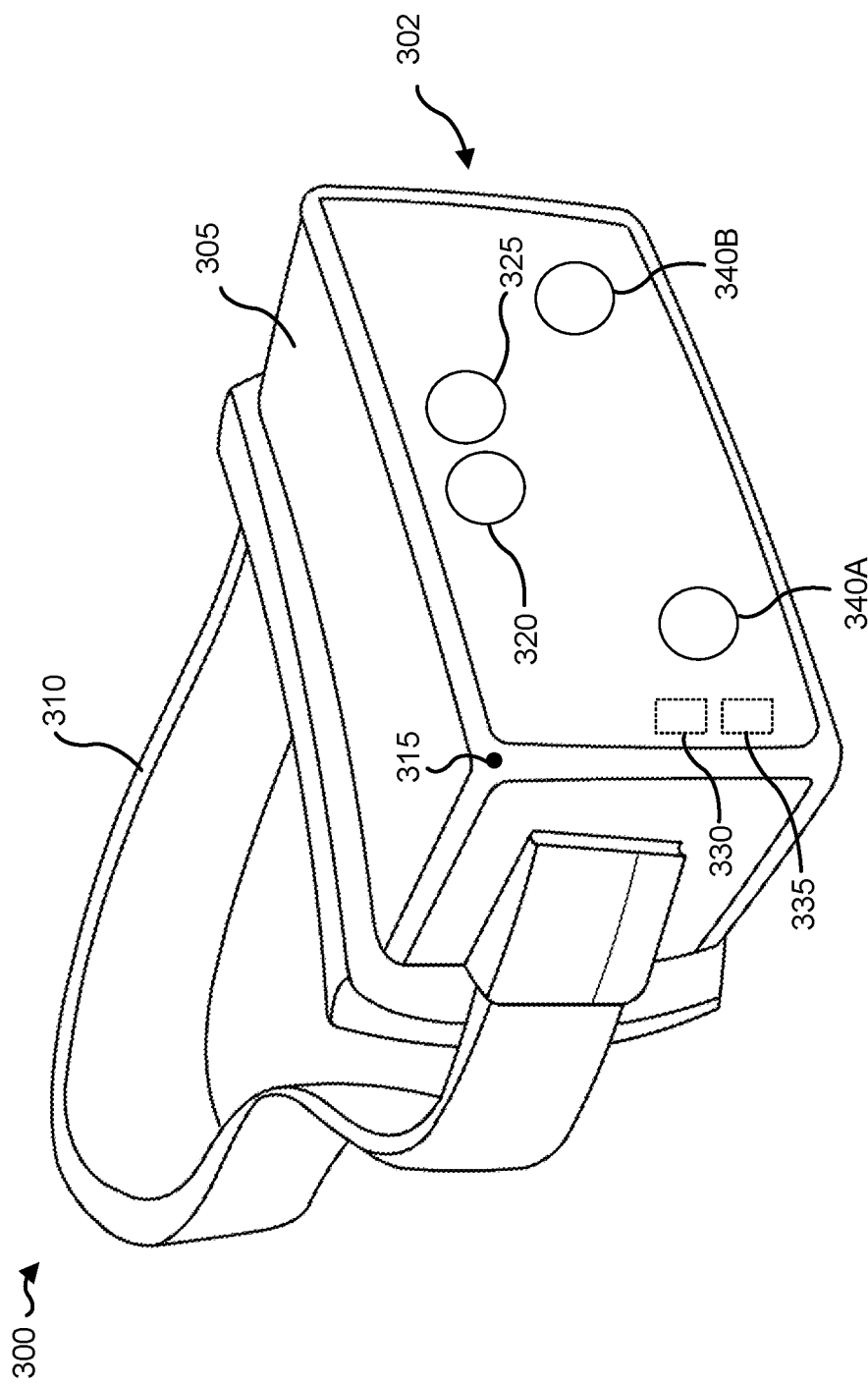
FIG. 3 is a perspective view of an exemplary HMD device that may be included in the HMD system of FIG. 2, according to aspects of the present disclosure.
Figure 4:
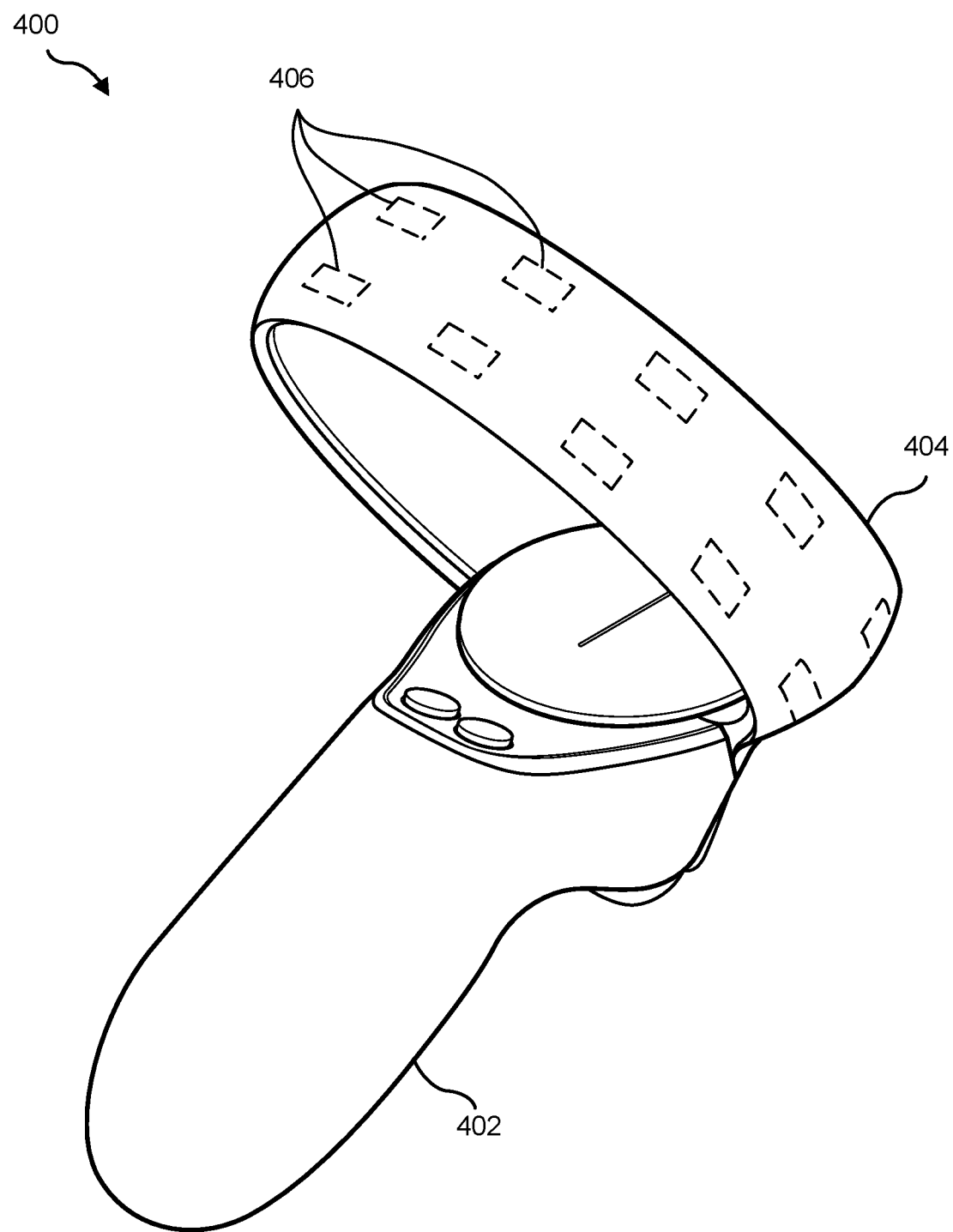
FIG. 4 is a perspective view of an exemplary hand-held controller that may be included in the HMD system of FIG. 2, according to aspects of the present disclosure.
Figure 7A:
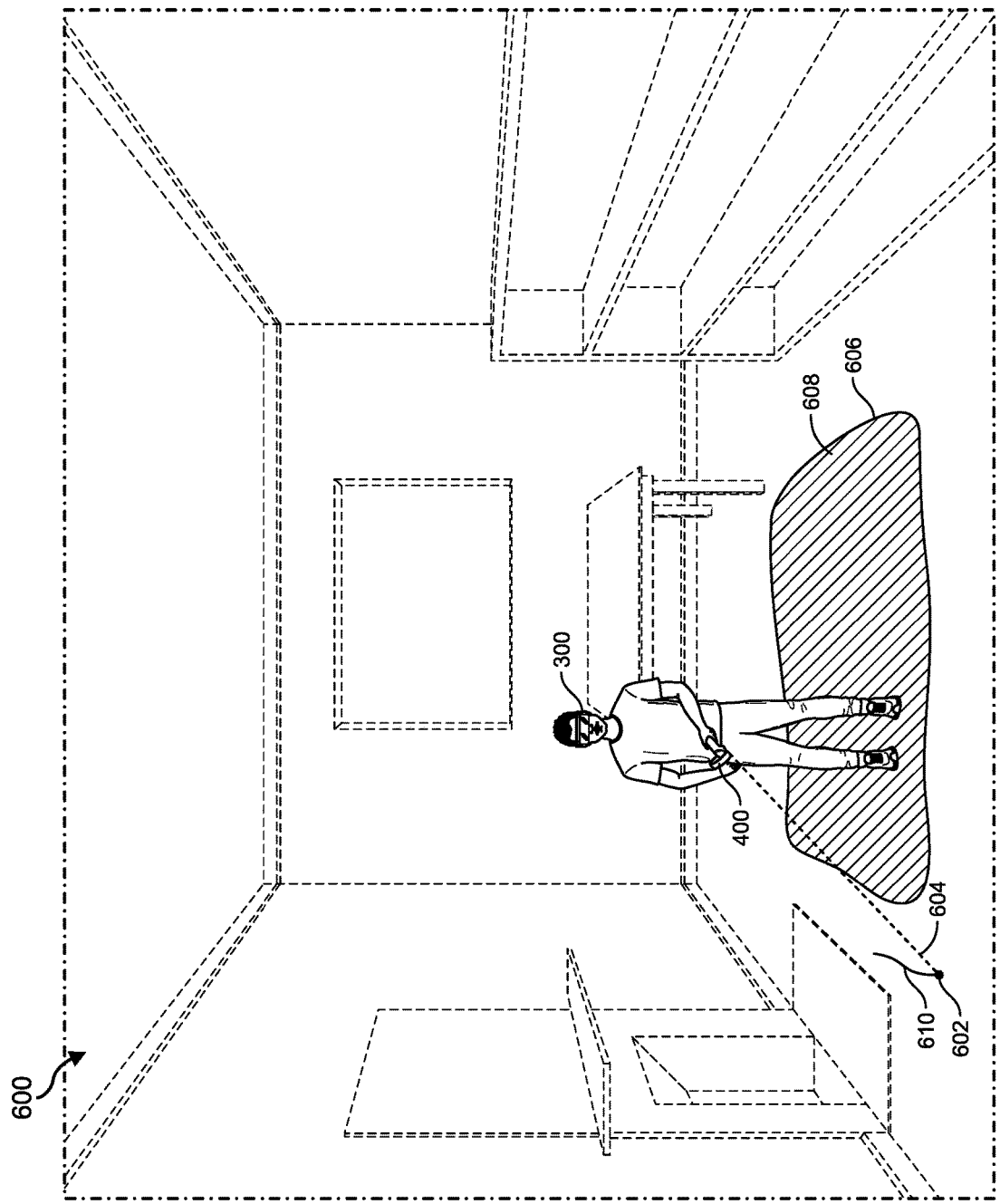
FIGS. 7A and 7B present a perspective view and top view, respectively, of a user continuing to interact with a reproduction of the real-world environment to produce a virtual boundary, according to aspects of the present disclosure.
Figure 7B:
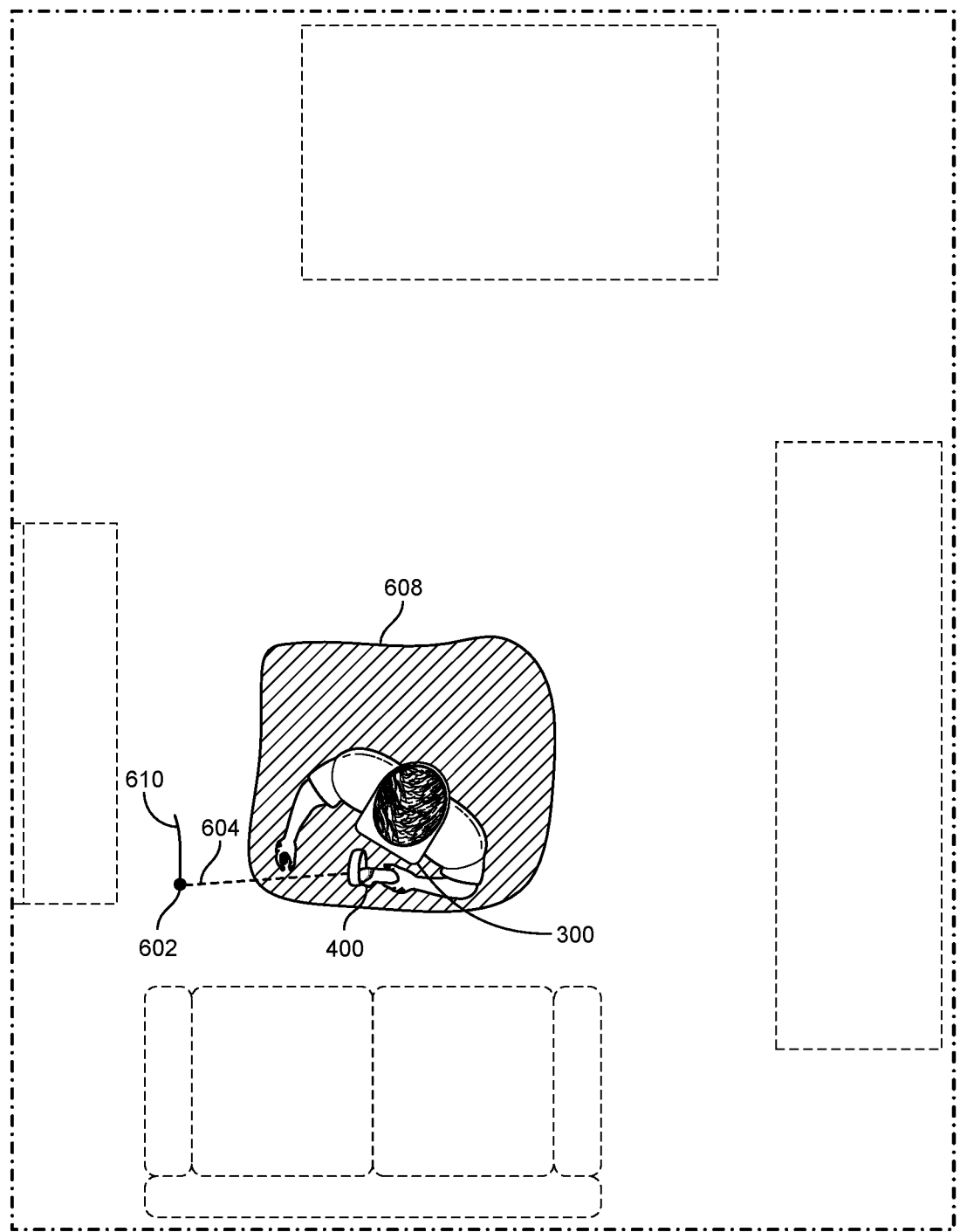
Figure 8A:
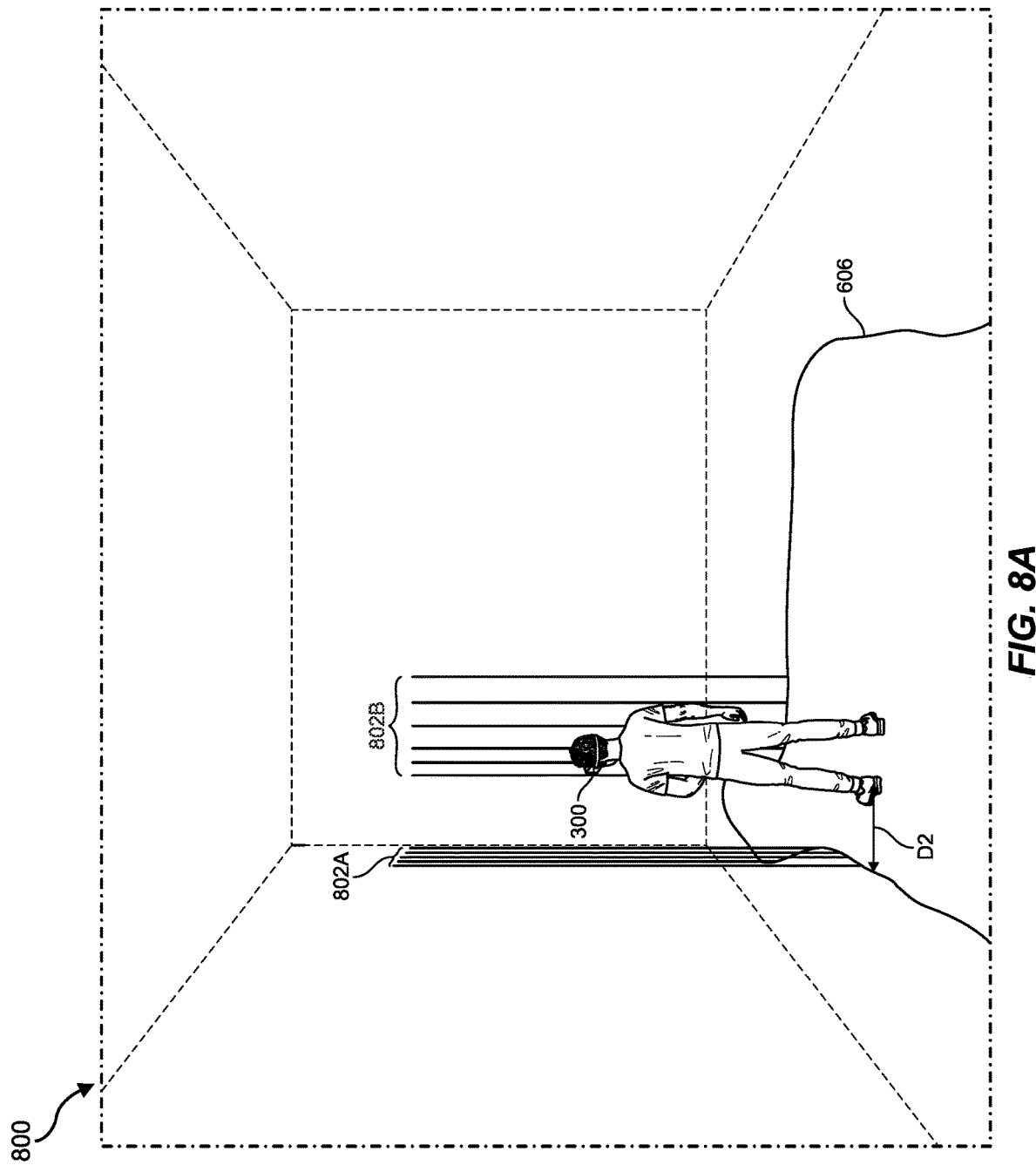
FIGS. 8A and 8B present a perspective view and top view, respectively, of a user interacting with a defined virtual boundary, according to aspects of the present disclosure.
Figure 8B:
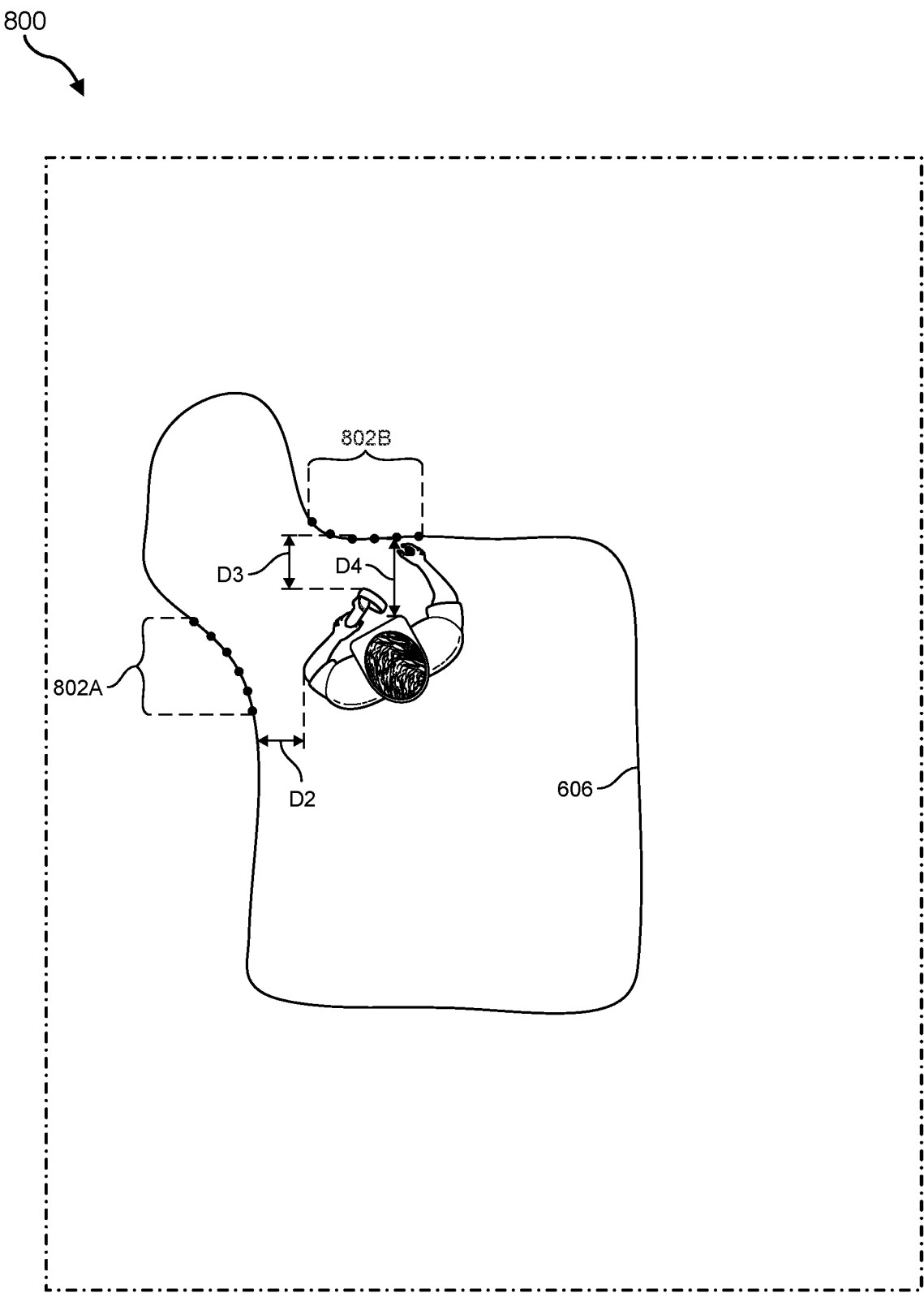
Figure 9:
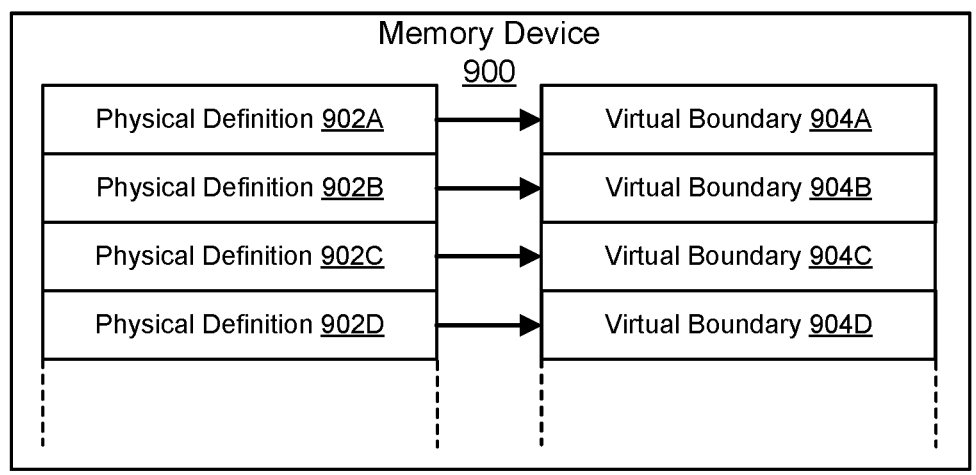
FIG. 9 is a diagram of a memory device containing a set of physical definitions that correspond to a set of pre-defined virtual boundaries, according to aspects of the present disclosure.

The following will provide, with reference to FIGS. 1-9, detailed descriptions of systems and methods that permit a user to modify his or her own virtual boundary, relative to the real-world environment, and to use that virtual boundary to provide a visual and/or aural indication to the user to make the user aware of the real-world environment whenever the risk of an accidental collision gets too high. FIG. 1 illustrates an exemplary process of modifying a virtual boundary. FIG. 2 illustrates an exemplary VR system. FIG. 3 illustrates an exemplary HMD device. FIG. 4 illustrates an exemplary direction indicator. FIGS. 5A-5B illustrate a user using an exemplary AR system. FIGS. 6A-6C illustrate how the user may interact with a reproduction of a real-world environment. FIGS. 7A-7B illustrate how the user may modify a virtual boundary. FIGS. 8A-8B illustrate how the user may interact with the virtual boundary. FIG. 9 illustrates an exemplary memory device of an VR system.

FIG. 1 is a flow diagram of an exemplary computer-implemented method 100 for modifying a virtual boundary. The steps shown in FIG. 1 may be performed by any suitable computer-executable code and/or computing system, including the system(s) illustrated in FIGS. 2-4. In one example, each of the steps shown in FIG. 1 may represent an algorithm whose structure includes and/or is represented by multiple sub-steps, examples of which will be provided in greater detail below.

As illustrated in FIG. 1, at step 110 one or more of the systems described herein may receive an indication of a reference elevation representing a plane of a real-world environment. For example, a processing subsystem 210 of an HMD system 200, as illustrated in FIG. 2, may receive an indication of the reference elevation.

In some embodiments, the term "reference elevation" may refer to an elevation corresponding to a reference plane in the real-world environment which may be used for determining points/locations pointed to by a direction indicator. In some embodiments, the reference elevation may be a baseline elevation corresponding to a base plane of the real-world environment. The term "base plane" may refer to a lowest elevation a user may encounter in the real-world environment. Examples of base planes include, without limitation, floors, tables, ground, etc. The baseline elevation may represent an elevation of the base plane and may be defined orthogonally to the floor. A virtual boundary for a VR system may be defined and/or modified with respect to the reference elevation and/or corresponding plane. FIG. 2 illustrates an exemplary VR system which may utilize virtual boundaries.

FIG. 2 is a block diagram of one embodiment of HMD system 200 that presents scenes (e.g., captured scenes, artificially-generated scenes, or a combination of the same) to a user. HMD system 200 may operate in a virtual reality (VR) system environment, an augmented reality (AR) system environment, a mixed reality (MR) system environment, or some combination thereof. HMD system 200 shown in FIG. 2 may include an HMD device 205 that includes or communicates with processing subsystem 210 and an input/output (I/O) interface 215. HMD device 205 may completely obstruct the user's view of the real-world environment, in some embodiments. Other embodiments may only partially obstruct the user's view of the real-world environment and/or may obstruct the user's view depending on content being displayed in a display of HMD device 205.

While FIG. 2 shows an exemplary HMD system 200 that includes at least one HMD device 205 and at least one I/O interface 215, in other embodiments any number of these components may be included in HMD system 200. For example, there may be multiple HMDs 205, each having an associated I/O interface 215, with each HMD device 205 and I/O interface 215 communicating with processing subsystem 210. In embodiments in which processing subsystem 210 is not included within or integrated with HMD device 205, HMD device 205 may communicate with processing subsystem 210 over a wired connection or a wireless connection. In alternative configurations, different and/or additional components may be included in HMD system 200. Additionally, functionality described in connection with one or more of the components shown in FIG. 2 may be distributed among the components in a different manner than described with respect to FIG. 2, in some embodiments.

HMD device 205 may present a variety of content to a user, including virtual views of an artificially rendered virtual-world environment and/or augmented views of a physical, real-world environment, augmented with computer-generated elements (e.g., two-dimensional (2D) or three-dimensional (3D) images, 2D or 3D video, sound, etc.). In some embodiments, the presented content includes audio that is presented via an internal or external device (e.g., speakers and/or headphones) that receives audio information from HMD device 205, processing subsystem 210, or both, and presents audio data based on the audio information. In some embodiments, such speakers and/or headphones may be integrated into or releasably coupled or attached to HMD device 205. HMD device 205 may include one or more bodies, which may be rigidly or non-rigidly coupled together. A rigid coupling between rigid bodies may cause the coupled rigid bodies to act as a single rigid entity. In contrast, a non-rigid coupling between rigid bodies may allow the rigid bodies to move relative to each other. An embodiment of HMD device 205 is an HMD device 300 shown in FIG. 3 and described in further detail below.

In some examples, HMD device 205 may include a depth-sensing subsystem 220 (or depth camera system), an electronic display 225, an image capture subsystem 230 that includes one or more cameras, one or more position sensors 235, and/or an inertial measurement unit (IMU) 240. Other embodiments of HMD device 205 may include an optional eye-tracking or gaze-estimation system configured to track the eyes of a user of HMD device 205 to estimate the user's gaze. An optional varifocal module may be configured to adjust the focus of one or more images displayed on electronic display 225 based on the determined eye-tracking information obtained from the eye-tracking system and other components. Some embodiments of HMD device 205 may have different components than those described in conjunction with FIG. 2.

Depth-sensing subsystem 220 may capture data describing depth information characterizing a local real-world area or environment surrounding some or all of HMD device 205 and/or characterizing a position, velocity, or position of depth-sensing subsystem 220 (and thereby of HMD device 205) within the local area. Depth-sensing subsystem 220 can compute the depth information using collected data (e.g., based on a captured light according to one or more computer-vision schemes or algorithms, by processing a portion of a structured light pattern, by time-of-flight (ToF) imaging, simultaneous localization and mapping (SLAM), etc.) or depth-sensing subsystem 220 can transmit this data to another device such as an external implementation of processing subsystem 210 that can determine the depth information using the data from depth-sensing subsystem 220.

Electronic display 225 may display two-dimensional or three-dimensional images to the user in accordance with data received from processing subsystem 210. In various embodiments, electronic display 225 includes a single electronic display or multiple electronic displays (e.g., a display for each eye of a user). Examples of electronic display 225 may include: a liquid crystal display (LCD), an organic light emitting diode (OLED) display, an inorganic light emitting diode (ILED) display, an active-matrix organic light-emitting diode (AMOLED) display, a transparent organic light emitting diode (TOLED) display, another suitable display, or some combination thereof. Electronic display 225 may be opaque such that the user cannot see the local environment through electronic display 225.

Image capture subsystem 230 may include one or more optical image sensors or cameras that capture and collect image data from a local environment. In some embodiments, the sensors included in image capture subsystem 230 may provide stereoscopic views of the local environment that may be used by processing subsystem 210 to generate image data that characterizes the local environment and/or a position and orientation of HMD device 205 within the local environment. For example, the image capture subsystem 230 may include simultaneous localization and mapping (SLAM) cameras or other cameras that include a wide-angle lens system that captures a wider field-of-view than may be captured by the eyes of the user. As described herein, the image capture subsystem 230 may provide pass-through views of the real-world environment that are displayed to the user via the electronic display 225 when HMD system 200 is in a boundary definition state.

In some embodiments, processing subsystem 210 may process the images captured by image capture subsystem 230 to remove distortion caused by the lens system of image capture subsystem 230 and/or by a separation distance between two image sensors that is noticeably larger than or noticeably less than an average separation distance between users' eyes. For example, when image capture subsystem 230 is, or is part of, a SLAM camera system, direct images from image capture subsystem 230 may appear distorted to a user if shown in an uncorrected format. Image correction or compensation may be performed by processing subsystem 210 to correct and present the images to the user with a more natural appearance, so that it appears to the user as if the user is looking through electronic display 225 of HMD device 205. In some embodiments, image capture subsystem 230 may include one or more image sensors having lenses adapted (in terms of field-of-view, separation distance, etc.) to provide pass-through views of the local environment. Image capture subsystem 230 may capture color image or monochromatic images.

IMU 240 may, in some examples, represent an electronic subsystem that generates data indicating a position and/or orientation of HMD device 205 based on measurement signals received from one or more of position sensors 235 and from depth information received from depth-sensing subsystem 220 and/or image capture subsystem 230. For example, a position sensor 235 may generate one or more measurement signals in response to motion of HMD device 205. Examples of position sensors 235 include: one or more accelerometers, one or more gyroscopes, one or more magnetometers, another suitable type of sensor that detects motion, a type of sensor used for error correction of IMU 240, or some combination thereof. Position sensors 235 may be located external to IMU 240, internal to IMU 240, or some combination thereof.

Based on the one or more measurement signals from one or more position sensors 235, IMU 240 may generate data indicating an estimated current position, elevation, and/or orientation of HMD device 205 relative to an initial position and/or orientation of HMD device 205. For example, position sensors 235 may include multiple accelerometers to measure translational motion (forward/back, up/down, left/right) and multiple gyroscopes to measure rotational motion (e.g., pitch, yaw, roll). As described herein, image capture subsystem 230 and/or depth-sensing subsystem 220 may generate data indicating an estimated current position and/or orientation of HMD device 205 relative to the real-world environment in which HMD device 205 is used.

I/O interface 215 may represent a subsystem or device that allows a user to send action requests and receive responses from processing subsystem 210 and/or a direction indicator 270. In some embodiments, direction indicator 270 may comprise a hand-held controller or other device that may be manipulated by the user to provide input, such as orientation and/or position data as sensed by sensors of direction indicator 270, to I/O interface 215. In other embodiments, direction indicator 270 may provide passive input to I/O interface 215. For example, direction indicator 270 may comprise the user's finger or hand, a glove or other wearable object, a hand-held object, the user's eyes and/or gaze, and/or another user-manipulatable object which may be detected by sensors of HMD system 200 to determine orientation and/or position data relative to direction indicator 270. In some embodiments, I/O interface 215 may facilitate communication with more than one direction indicator 270. For example, the user may have two direction indicators 270, one in each hand. An action request may, in some examples, represent a request to perform a particular action. For example, an action request may be an instruction to start or end capture of image or video data or an instruction to perform a particular action within an application or to start or end a boundary definition state. I/O interface 215 may include one or more input devices or enable communication with one or more input devices. Exemplary input devices may include a keyboard, a mouse, a hand-held controller, or any other suitable device for receiving action requests and communicating the action requests to processing subsystem 210.

An action request received by I/O interface 215 may be communicated to processing subsystem 210, which may perform an action corresponding to the action request. In some embodiments, direction indicator 270 includes an IMU 240 that captures inertial data indicating an estimated position of direction indicator 270 relative to an initial position. In some embodiments, I/O interface 215 and/or direction indicator 270 may provide haptic feedback to the user in accordance with instructions received from processing subsystem 210 and/or HMD device 205. For example, haptic feedback is provided when an action request is received or processing subsystem 210 communicates instructions to I/O interface 215 causing I/O interface 215 to generate or direct generation of haptic feedback when processing subsystem 210 performs an action.

Processing subsystem 210 may include one or more processing devices or physical processors that provide content to HMD device 205 in accordance with information received from one or more of: depth-sensing subsystem 220, image capture subsystem 230, I/O interface 215, and direction indicator 270. In the example shown in FIG. 2, processing subsystem 210 includes an engine 260, an application store 250, and a tracking module 255. Some embodiments of processing subsystem 210 have different modules or components than those described in conjunction with FIG. 2. Similarly, the functions further described below may be distributed among the components of HMD system 200 in a different manner than described in conjunction with FIG. 2.

Application store 250 may store one or more applications for execution by processing subsystem 210. An application may, in some examples, represent a group of instructions, that when executed by a processor, generates content for presentation to the user. Content generated by an application may be generated in response to inputs received from the user via movement of HMD device 205 or direction indicator 270. Examples of applications include: gaming applications, conferencing applications, video playback applications, or other suitable applications.

Tracking module 255 may calibrate HMD system 200 using one or more calibration parameters and may adjust one or more calibration parameters to reduce error in determination of the position of HMD device 205 or direction indicator 270. For example, tracking module 255 may communicate a calibration parameter to depth-sensing subsystem 220 to adjust the focus of depth-sensing subsystem 220 to more accurately determine positions of structured light elements captured by depth-sensing subsystem 220. Calibration performed by tracking module 255 may also account for information received from IMU 240 in HMD device 205 and/or another IMU 240 included in direction indicator 270. Additionally, if tracking of HMD device 205 is lost (e.g., depth-sensing subsystem 220 loses line of sight of at least a threshold number of structured light elements), tracking module 255 may recalibrate some or all of HMD system 200.

Tracking module 255 may track movements of HMD device 205 or of direction indicator 270 using information from depth-sensing subsystem 220, image capture subsystem 230, one or more position sensors 235, IMU 240, or some combination thereof. For example, tracking module 255 may determine a position of a reference point of HMD device 205 in a mapping of the real-world environment based on information collected with HMD device 205. Additionally, in some embodiments, tracking module 255 may use portions of data indicating a position and/or orientation of HMD device 205 and/or direction indicator 270 from IMU 240 to predict a future position and/or orientation of HMD device 205 and/or direction indicator 270. Tracking module 255 may also provide the estimated or predicted future position of HMD device 205 or I/O interface 215 to engine 260.

In some embodiments, tracking module 255 may track other features that can be observed by depth-sensing subsystem 220, image capture subsystem 230, and/or by another system. For example, tracking module 255 may track one or both of the user's hands so that the location of the user's hands within the real-world environment may be known and utilized. Tracking module 255 may receive and process data in order to determine a pointing direction of a finger of one of the user's hands, for instance when direction indicator 270 comprises the user's hands. Tracking module 255 may also receive information from one or more eye-tracking cameras included in some embodiments of HMD device 205 to tracking the user's gaze.

Image processing engine 260 may generate a three-dimensional mapping of the area surrounding some or all of HMD device 205 (i.e., the "local area" or "real-world environment) based on information received from HMD device 205. In some embodiments, engine 260 determines depth information for the three-dimensional mapping of the local area based on information received from depth-sensing subsystem 220 that is relevant for techniques used in computing depth. Engine 260 may calculate depth information using one or more techniques in computing depth from structured light. In various embodiments, engine 260 uses the depth information to, e.g., update a model of the local area, and generate content based in part on the updated model.

Engine 260 may also execute applications within HMD system 200 and receive position information, acceleration information, velocity information, predicted future positions, or some combination thereof, of HMD device 205 from tracking module 255. Based on the received information, engine 260 may determine content to provide to HMD device 205 for presentation to the user. For example, if the received information indicates that the user has looked to the left, engine 260 generates content for HMD device 205 that corresponds to the user's movement in a virtual environment or in an environment augmenting the local area with additional content. Additionally, engine 260 may perform an action within an application executing on processing subsystem 210 in response to an action request received from I/O interface 215 and/or direction indicator 270 and provide feedback to the user that the action was performed. The provided feedback may be visual or audible feedback via HMD device 205 or haptic feedback via direction indicator 270.

Returning to FIG. 1, the systems described herein may perform step 110 in a variety of ways. In one example, the reference elevation may have been previously established and stored. In other examples, the reference elevation may be set by the user, such as by using HMD device 300 and/or a hand-held controller 400 to define and/or confirm the reference elevation. For example, HMD system 200 may receive an indication of the reference elevation from HMD device 300 and/or hand-held controller 400.

FIG. 3 is a diagram of HMD device 300, in accordance with one embodiment of HMD device 205. HMD device 300 may include an imaging subsystem and a depth-sensing subsystem. HMD device 300 may be part of, e.g., a VR system, an AR system, an MR system, or some combination thereof. In embodiments that describe an AR system and/or an MR system, portions of a front side 302 of HMD device 300 are at least partially transparent in the visible band (about 380 nanometers (nm) to 750 nm). More specifically, portions of HMD device 300 that are between front side 302 of HMD device 300 and an eye of the user may be at least partially transparent (e.g., a partially-transparent electronic display 225). In other embodiments, front side 302 is opaque, preventing the user from seeing the real-world environment. HMD device 300 may include a front rigid body 305 housing the electronic display 225 and other components, a user attachment system such as a band 310 that secures HMD device 300 to a user's head, and a reference point 315 that can characterize a position and/or orientation of HMD device 300.

In addition, HMD device 300 may include an imaging aperture 320 and an illumination aperture 325. An illumination source included in depth-sensing subsystem 220 may emit light (e.g., structured light) through illumination aperture 325. An imaging device of depth-sensing subsystem 220 may capture light from the illumination source that is reflected or backscattered from the local area through imaging aperture 320. Embodiments of HMD device 300 may further include cameras 340A and 340B that may be components of image capture subsystem 230 of FIG. 2. Cameras 340A and 340B may be separated from each other by a distance that is different than the average separation distance between users' eyes.

Front rigid body 305 may include one or more electronic display elements, one or more integrated eye-tracking systems, an IMU 330, one or more position sensors 335, and reference point 315. IMU 330 may represent an electronic device that generates fast calibration data based on measurement signals received from one or more of position sensors 335. A position sensor 335 may generate one or more measurement signals in response to motion of HMD device 300.

FIG. 4 is a perspective view of an exemplary hand-held controller 400 that may be an embodiment of direction indicator 270 included in HMD system 200 of FIG. 2, in accordance with some embodiments. HMD system 200 may include one or more hand-held controllers like controller 400. For example, HMD system 200 may include two hand-held controllers 400, with one hand-held controller 400 for each of a user's right and left hands. Each hand-held controller 400 may be communicatively coupled to HMD device 205 and/or to a computing device (e.g., a personal computer, processing subsystem 210, etc.). Hand-held controller 400 may be communicatively coupled to HMD device 205 via any suitable wireless and/or wired connection.

As shown in FIG. 4, hand-held controller 400 may include a grip 402 sized to fit within a user's hand. Hand-held controller 400 may also include a tracking loop 404 for tracking position, orientation, and/or movement of hand-held controller 400 with respect to HMD device 205 and/or with respect to the real-world environment. In some embodiments, tracking loop 404 may include one or more tracking lights, such as an array of tracking lights 406. The array of tracking lights 406 may include tracking LEDs (e.g., infrared (IR) LEDs) that are used for motion and positional tracking purposes to provide 360-degree motion control while using HMD system 200. Tracking lights 406 may be utilized to determine an orientation of controller 400 so that an intersection point with the floor of the real-world environment can be identified in order to "draw" a virtual boundary. Controller 400 may include tracking lights on any suitable portion of controller 400. In some examples, tracking lights 406 of hand-held controller 400 may emit light having wavelengths greater than approximately 700 nm and less than approximately 900 nm. In one embodiment, tracking lights 406 of hand-held controller 400 may emit light having a wavelength of approximately 850 nm (e.g., between approximately 840 nm and 860 nm or between approximately 830 nm and 870 nm). In at least one embodiment, cameras 340A and 340B may receive light emitted by the tracking lights 406 on hand-held controller 400, and tracking module 255 may utilize the received light to determine location, orientation, and/or movement of hand-held controller 400 relative to HMD device 205 and/or another reference frame, such as a reference frame of the real-world environment.

To define the reference elevation, the user may interact with HMD system 200. For example, the user may be prompted to position hand-held controller 400 in contact with a floor, which may provide the base plane of the real-world environment. The reference elevation may be defined orthogonally to the floor. In some embodiments, a component of HMD device 300 may determine a height above the floor based on an orientation of HMD device 300 and one or more depth measurements characterizing the distance from HMD device 300 to the floor. For instance, HMD system 200 may prompt the user to look at the floor of the real-world environment as part of a virtual boundary definition process.

Some embodiments may further include receiving a confirmation of the reference elevation. The user may be presented with an indication of the reference elevation. For instance, HMD system 200 may show a visual representation of the plane associated with the reference elevation and/or a current height of HMD device 300 from the reference elevation. The user may then confirm the reference elevation or define/redefine the reference elevation as described above.

Returning to FIG. 1, at step 120 one or more of the systems described herein may establish, with respect to the reference elevation, a virtual boundary for a virtual-world environment. For example, processing subsystem 210 and/or HMD device 205 and/or HMD device 300 may determine the virtual boundary based on input from direction indicator 270 and/or controller 400 or based on retrieving a previously-defined virtual boundary.

In some embodiments, the term "virtual boundary" may refer to a boundary defined relative to the user's real-world environment and/or a virtual environment. Examples of virtual boundaries include, without limitation, a safety boundary as described herein which may define a safe distance away from obstacles in the real-world environment that the user may encounter during VR and/or AR experiences. Other virtual boundaries may include boundaries indicating ideal locations for being detected by sensors, boundaries for restricting movement of the user in the real-world environment, boundaries which may be used for placing and/or clearing obstacles in the virtual environment, and boundaries for other uses.

The systems described herein may perform step 120 in a variety of ways. In one example, the virtual boundary may be loaded from a previously stored setting, such as a default setting or previous user action stored in HMD system 200. In other examples, the user may define the virtual boundary using, for example, HMD system 200.

Figure 5A:
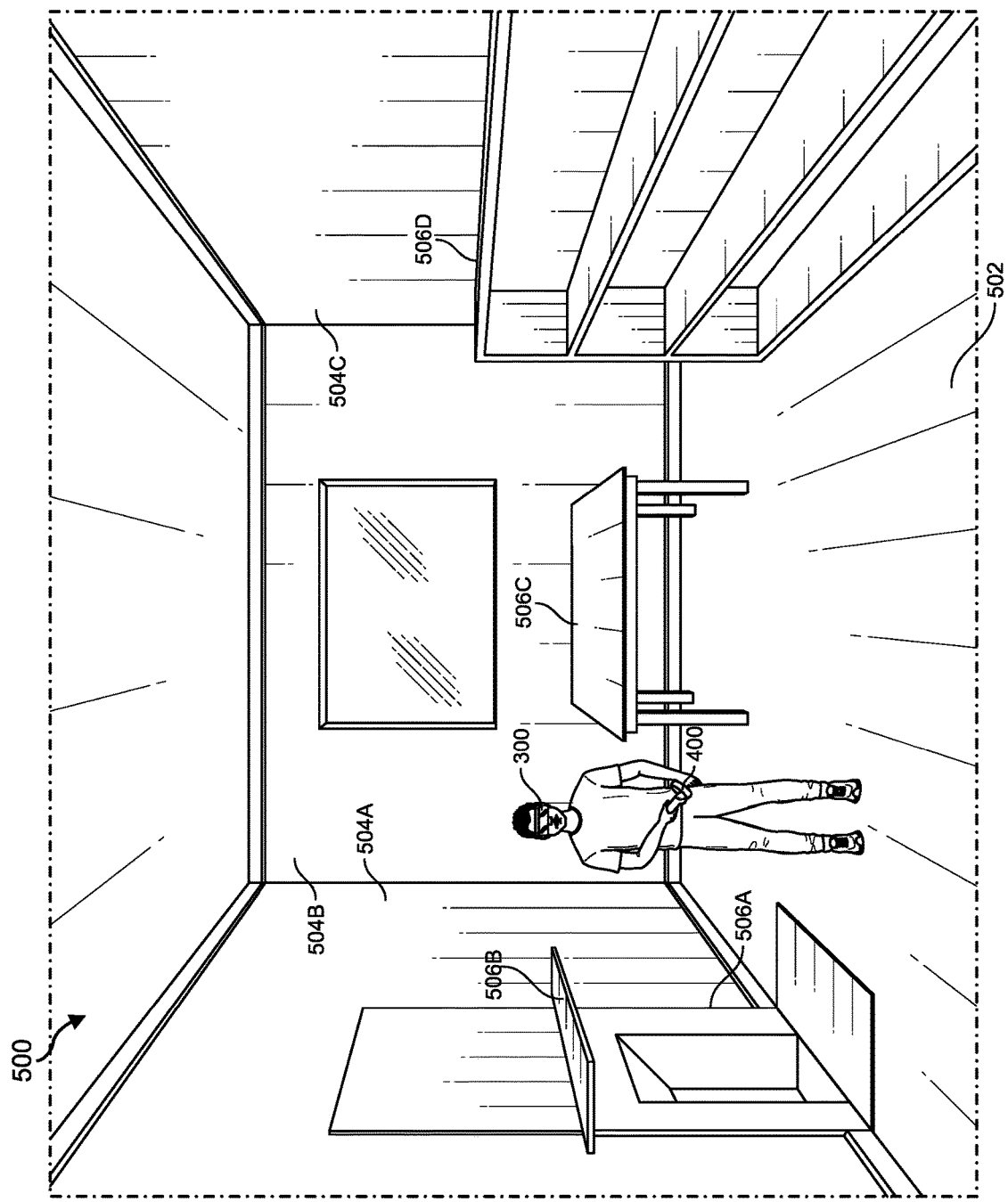
FIGS. 5A and 5B present a perspective view and a top view, respectively, of a user wearing the HMD device of FIG. 3 and holding the hand-held controller of FIG. 4 in a real-world environment, according to aspects of the present disclosure.
Figure 5B:
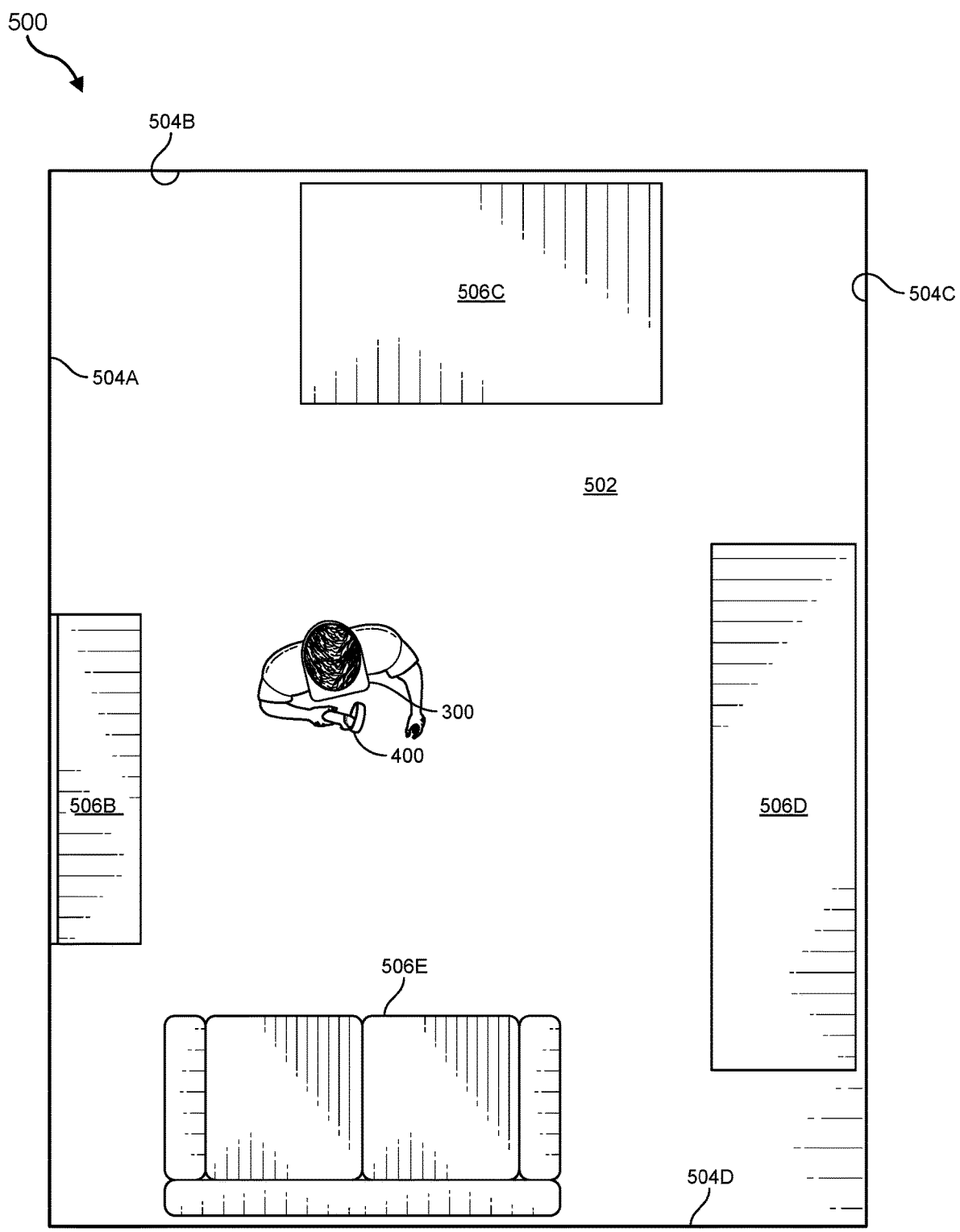

FIGS. 5A and 5B present a perspective view and a top view, respectively, of a user wearing HMD device 300 of FIG. 3 and holding hand-held controller 400 of FIG. 4 in a real-world environment 500, such as a living room, according to some embodiments. Real-world environment 500 may include a base plane 502, also referred to as a floor 502, and walls 504A, 504B, 504C, and 504D, collectively referred to as walls 504. Real-world environment 500 may further include a plurality of objects or features within the room that pose a collision risk when the user's view is obstructed by HMD device 300. For example, environment 500 may include a fireplace 506A having a protruding mantelpiece 506B, a table 506C, and shelves 506D. Environment 500 may further include a sofa 506E, as shown in FIG. 5B. The objects and features 506A, 506B, 506C, 506D, and 506E may be referred to, along with walls 504, as features 506 of real-world environment 500.

In some embodiments, the user may move within real-world environment 500 in order to move within a virtual environment displayed in HMD device 300. In other words, as the user moves within real-world environment 500, the images shown in electronic display 225 of HMD device 300 may be updated based on the user's movements. Accordingly, the user moves relative to the virtual environment as the user moves in real-world environment 500. As described in greater detail below, embodiments of the systems and methods described herein may enable the user to define a virtual boundary that can be used to prevent the user from colliding with any of features 506 when the user cannot see the real-world environment (due to, e.g., obstruction of the user's real-world view by HMD device 300).

Figure 6A:
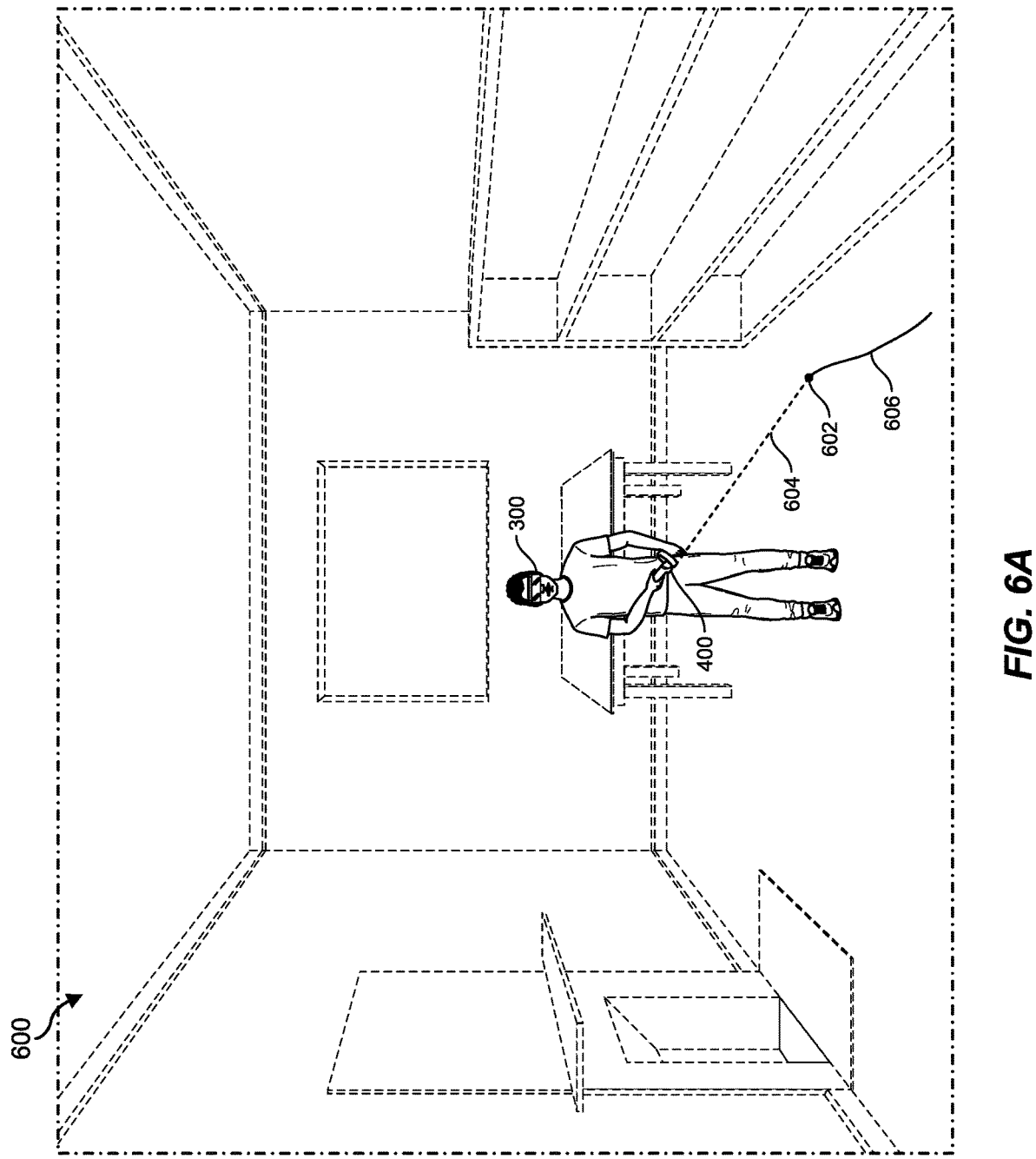
FIGS. 6A and 6B present a perspective view and top view, respectively, of a user interacting with a reproduction of the real-world environment to produce a virtual safety boundary, according to aspects of the present disclosure.
Figure 6B:
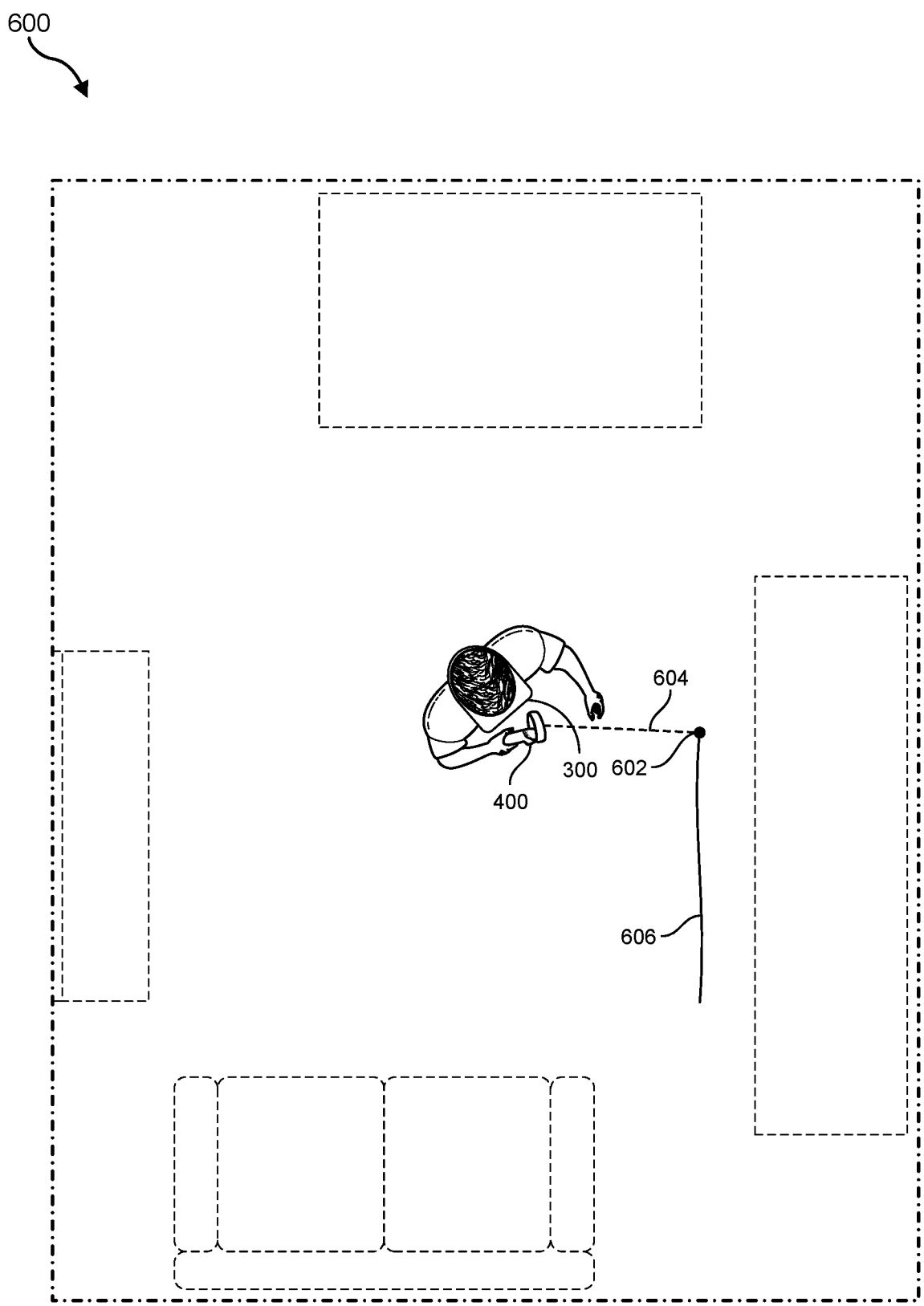

FIGS. 6A and 6B present a perspective view and top view, respectively, of a user interacting with a reproduction 600 of real-world environment 500 of FIGS. 5A and 5B to produce a virtual boundary or safety boundary, according to some embodiments. Because the user's view of real-world environment 500 may be totally or partially obstructed by HMD device 300, reproduction 600 of real-world environment 500 may be provided to the user in electronic display 225 of HMD device 300. Reproduction 600 may be produced by image capture subsystem 230 to provide a pass-through view of real-world environment 500. In some embodiments, processing subsystem 210 may perform image correction to images captured by image capture subsystem 230 to remove distortions and provide an improved view of real-world environment 500. For example, the processing subsystem 210 may perform image correction to mitigate distortion caused by the lenses of cameras 340A and 340B and/or by the separation distance between cameras 340A and 340B.

As shown in FIGS. 6A, the user may utilize controller 400 as a pointer or direction indicator to select an intersection point 602, during a boundary definition state during which the user may define the virtual boundary. Intersection point 602 may be defined as the location of an intersection between floor 502 and a virtual line 604 that is defined by the orientation and position of controller 400, which is held and manipulated by the user. Virtual line 604 may be displayed to the user in HMD device 300 so that the user can draw out a virtual boundary 606 on floor 502. As the user manipulates controller 400, a series of intersection points like, intersection point 602, can be combined to form virtual boundary 606 that extends along floor 502. FIG. 6B illustrates a top view within reproduction 600 of real-world environment 500 that depicts intersection point 602, virtual line 604, and virtual boundary 606.

Figure 6C:
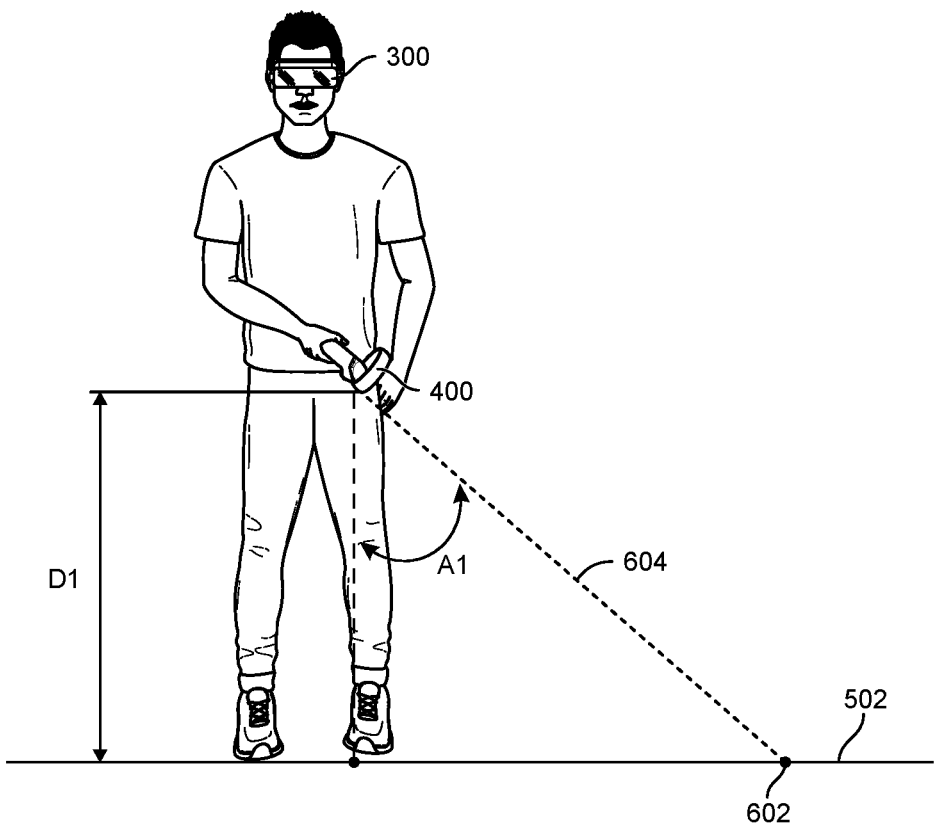
FIG. 6C is a diagram depicting a system for interacting with the real-world environment to define a virtual boundary, according to aspects of the present disclosure.

FIG. 6C is a diagram showing how intersection point 602 may be defined, according to some embodiments. The position and orientation of the hand-held controller within real-world environment 500 may be determined based on subsystems included within hand-held controller 400, such as an IMU and/or position trackers. In some instances, the user may be instructed by a message displayed in HMD device 300 to place hand-held controller 400 into contact with base plane or floor 502 to prepare for a boundary definition process. The user may then activate a button on controller 400 or hold controller 400 still for a predetermined amount of time to indicate to HMD system 200 that controller 400 is in contact with floor 502. The user may then be directed to stand, causing both HMD device 300 and controller 400 to be displaced away from floor 502 by a displacement D1, which may be used as a height or elevation of controller 400 of floor 502. In some embodiments, HMD device 300 may determine its elevation above floor 502 and a distance between HMD device 300 and hand-held controller 400. For example, depth-sensing subsystem 220 may determine the distance from floor 502 to HMD device 300 using structured light or by a triangulation estimation using stereoscopic images. The distance between HMD device 300 and hand-held controller 400 may be subtracted from the height of HMD device 300 above floor 502 to determine the displacement D1 or the elevation of hand-held controller 400. The orientation of controller 400 may be used to determine an angle A1 that an axis of controller 400 makes with floor 502. Using the location of controller 400, the displacement D1, and the angle A1, the point of intersection between virtual line 604 and floor 502 may be used as intersection point 602. By manipulating controller 400, a plurality of intersection points 602 may be identified and these points 602 may be connected to form virtual boundary 606. Although FIG. 6C illustrates floor 502 as the reference elevation, in other embodiments the reference elevation may be defined with respect to another plane in the real-world environment.

Turning back to FIG. 1, at step 130 one or more of the systems described herein may receive a request from a user to modify the virtual boundary. For example, HMD system 200 may receive the request to modify the virtual boundary from the user via controller 400.

In some embodiments, HMD system 200 may enter a boundary modification state to monitor inputs for modifying the virtual boundary. The term "boundary modification state" may refer to a state or phase during which the virtual boundary may be modified by the user. The boundary modification state may be the same or similar phase as a boundary definition state during which the virtual boundary may be defined, or a separate phase. The boundary modification state may be a specific mode of HMD system 200 exclusively for modifying the virtual boundary. Alternatively, the boundary modification state may be incorporated with other states of operation of HMD system 200.

The systems described herein may perform step 130 in a variety of ways. In one example, the user may be notified that the virtual boundary may be inadequate, and the user may accordingly initiate the boundary modification state. The user may be notified as to the inadequacy of the virtual boundary in various ways. For example, the user may receive a visual or audible notification, such as through HMD device 300. The notification may be an icon or may be a more robust visual indicator.

In some examples, the system may also capture a view of the real-world environment with an imaging system of a head-mounted display system. The captured view may have lens-induced distortion. The system may correct the lens-induced distortion in the captured view to produce a compensated view of the real-world environment. The system may superimpose the virtual boundary on the compensated view of the real-world environment and display the compensated view of the real-world environment in a display of the head-mounted display system during the boundary modification state. FIGS. 7A and 7B illustrate an exemplary scenario of the compensated view of the real-world environment presented to a user.

FIGS. 7A and 7B present a perspective view and top view, respectively, of a user interacting with reproduction 600 of the real-world environment 500 to produce the virtual boundary 606, according to some embodiments. Virtual boundary 606 may define a boundary region 608. Boundary region 608 may be displayed, for example by HMD device 300, as a filled-in shape defined by virtual boundary 606. Boundary region 608 may be displayed similar to virtual boundary 606, such as a solid color, or may be a shaded or semi-transparent color corresponding to virtual boundary 606.

In some examples, an area defined by virtual boundary 606, e.g., boundary region 608, may be compared against a minimum area threshold. The minimum area threshold may correspond to a minimum area, such as a minimum square footage, in which the user may be expected to safely operate VR and/or AR systems in the real-world environment. The minimum area threshold may be a predetermined or default value or may be dynamically determined in the real-world environment. The minimum area threshold may include dimension limits, such as a minimum and/or maximum length and/or width.

In some examples, the minimum area threshold may be explicitly presented to the user, such as an amount of square footage to be met or needed for the minimum area threshold. In other examples, the minimum area threshold may be represented by displaying the boundary region in a success color when the minimum area threshold is satisfied, or a warning color if the minimum area threshold is not satisfied. For example, virtual boundary 606 and/or boundary region 608 may be displayed in green when the minimum area threshold is satisfied and in red when the minimum area threshold is not satisfied.

Upon seeing that virtual boundary 606 does not satisfy the minimum area threshold, the user may initiate the boundary modification state to modify the virtual boundary. Alternatively, the boundary modification state may be automatically initiated if the minimum area threshold is not satisfied. For instance, during the boundary definition state, if virtual boundary 606 does not satisfy the minimum area threshold, the boundary modification state may be automatically initiated. In addition, the user may initiate the boundary modification state for other reasons. For example, the real-world environment may have changed, or the user may wish to tweak the virtual boundary such as if the user prefers a smaller or larger boundary region.

Returning to FIG. 1, at step 140 one or more of the systems described herein may, in response to the request from the user, monitor an orientation of a direction indicator to generate orientation data. For example, processing subsystem 210 and/or HMD device 205 and/or HMD device 300 may determine the orientation data based on input from direction indicator 270 and/or controller 400. In some examples, the orientation data may include and/or be associated with additional input data. For instance, the orientation data may include elevation data of the direction indicator with respect to the reference elevation. The orientation data may include position data of the direction indicator.

The systems described herein may perform step 140 in a variety of ways. In one example, the position and orientation of hand-held controller 400 within real-world environment 500 may be determined based on subsystems included within hand-held controller 400, such as an IMU and/or position sensors. As described above with respect to FIG. 6C, D1 may be monitored to determine the elevation data, and A1 may be monitored to determine the orientation data. Alternatively, the elevation data and orientation data may be determined from sensors external to controller 400, such as cameras viewing controller 400 in real-world environment 500.

Returning to FIG. 1, at step 150 one or more of the systems described herein may modify the virtual boundary based on the reference elevation and the orientation data. For example, processing subsystem 210 and/or HMD device 205 and/or HMD device 300 may modify the virtual boundary based on the elevation data and orientation data from direction indicator 270 and/or controller 400, and the reference elevation.

The systems described herein may perform step 150 in a variety of ways. In one example, an intersection between the plane and a virtual line that extends from the user device at the elevation indicated by the elevation data and at the orientation indicated by the orientation data may be determined. As illustrated in FIG. 6C, the location of controller 400, D1, and A1 may define where virtual line 604 begins, and the point of intersection between virtual line 604 and floor 502 may define intersection point 602. Similar to how a plurality of intersection points 602 may define virtual boundary 606, modifications to virtual boundary 606 may be defined by one or more intersection points 602. The intersection points 602 may define extensions to virtual boundary 606.

The virtual boundary may be modified in various ways. For example, FIGS. 7A and 7B illustrate how virtual boundary 606 may be modified. Virtual boundary 606 may not satisfy the minimum area threshold, and boundary region 608 may be displayed in the warning color. The user may manipulate controller 400 to define a modification line 610, which may be defined by one or more intersection points 602. Although not shown completed in FIGS. 7A and 7B, modification line 610 may outline a region that envelopes boundary region 608 in order to satisfy the minimum area threshold.

The virtual boundary may be modified by adding portions to the virtual boundary. For example, portions of virtual boundary 606 may be extended to add additional regions to boundary region 608. The additional regions may be connected to boundary region 608, such as connected to a side of boundary region 608, or may be a disconnected or otherwise discontinuous region associated with boundary region 608. The additional regions may partially or fully envelope boundary region 608.

In other examples, modifying the virtual boundary may include subtracting portions from the virtual boundary. For example, the boundary modification state may include an addition state for adding portions and a subtraction state for removing portions from the virtual boundary. The user may toggle between the addition and subtraction states to define and modify the virtual boundary to a desired shape. For instance, the user may use controller 400 to enter the addition state and draw additions to virtual boundary 606. The user may use controller 400 to enter the subtraction state and carve out portions from virtual boundary 606.

In yet other examples, modifying the virtual boundary may be accomplished by resetting the virtual boundary. For example, the user may send an indication to reset the virtual boundary. The user may then define the virtual boundary from an empty state. Alternatively, the user may be able to undo/redo one or more modifications.

The modified virtual boundary may be compared against the minimum area threshold. The comparison may occur dynamically, for example in real-time as the user draws modifications. Incomplete loops and/or unconnected portions may be automatically connected, for example with a shortest distance straight line for connecting unconnected portions, for the purposes of estimating area. Thus, the user may see in real-time when the minimum area threshold is satisfied. Alternatively, the minimum area comparison may occur when the user indicates terminating the boundary modification state. In some examples, the user may not terminate the boundary modification state unless the minimum area threshold is satisfied.

In addition, when the boundary modification state is terminated, the virtual boundary may be checked for errors. Errors may include, for example, unclosed loops, zero-area portions, portions that may be too small for users to reasonably use (which may be compared against a minimum portion area threshold), and other errors. In some examples, the errors may be automatically corrected. For instance, unclosed loops may be connected, problematic portions may be removed, etc. In other examples, the user may be alerted as to errors, and in some examples the boundary modification state may be automatically re-initiated. In some examples, the boundary modification state may not be terminated until there are no errors detected in the virtual boundary.

After the user completes the boundary modification state and finalizes the virtual boundary, which may require satisfying the minimum area threshold, the user may interact with the virtual boundary. FIGS. 8A and 8B present a perspective view and top view, respectively, of a user interacting with a defined virtual boundary in a virtual environment, according to some embodiments. As shown in FIGS. 8A and 8B, a virtual environment 800 may be displayed to the user in HMD device 300. Virtual environment 800 may represent a captured scene in which the user can move or an artificial environment such as in a video game. The user may move within virtual environment 800 by moving within real-world environment 500. The virtual environment may include a visual indication of virtual boundary 606. In other words, virtual boundary 606 may be visibly rendered and presented to the user so that the user is able to see virtual boundary 606 whenever the field of view of HMD device 300 includes virtual boundary 606. In some embodiments, the user may select a setting to have virtual boundary 606 consistently appear or to have virtual boundary 606 only appear when the user is within a threshold distance. Such a threshold distance may depend on the velocity or the user's movements and/or on the particular portion of the user or HMD system 200 that is closest to the boundary.

In some embodiments, when the user approaches virtual boundary 606, a boundary wall 802 (illustrated as elements 802A and 802B) may be rendered in HMD device 300 to alert the user to his or her proximity to virtual boundary 606 and, consequently, to feature 506 within real-world environment 500 that poses a collision risk. Boundary wall 802 may be rendered as a series of vertical or horizontal bars, a grid of lines, a grid of dots, etc., that may permit the user to continue to view a portion of virtual environment 800 through boundary wall 802. In other embodiments, boundary wall 802 may be rendered in a manner that completely "blocks" the user's view of a portion of virtual environment 800. In some embodiments, the rendering of boundary wall 802 may obstruct an increasing amount of the user's view as the user gets closer to virtual boundary 606. In other examples, boundary wall 802 may be overlaid or otherwise rendered on top of a pass-through view of the real-world environment (provided, for example, by image capture subsystem 230).

As shown in FIGS. 8A and 8B, separate wall portions may be rendered in HMD device 300. Accordingly, boundary wall 802A and boundary wall 802B are shown. Boundary wall 802A may be rendered when the distance between the user and virtual boundary 606 is less than or equal to a distance D2. The distance D2 may be configurable by the user or automatically by HMD system 200. For example, a threshold distance between 2 and 5 feet may be used in some embodiments. The threshold distance may be a function of the user's velocity, in some embodiments. Boundary wall 802B may be rendered in HMD device 300 based on the distance D3 between controller 400 and virtual boundary 606 or based on the distance D4 between HMD device 300 and virtual boundary 606. In some implementations, the position of the user's hands may be monitored and boundary wall 802 may be displayed to the user when the user's hand or hands are determined to be too close to virtual boundary 606, whether or not the user is holding one or more controllers 400.

In some embodiments, the method 100 may further include operations of generating a physical definition of the real-world environment and storing, in a memory device, the virtual boundary, including any modifications, in association with the physical definition of the real-world environment in which the virtual boundary was defined, so that a user-defined virtual boundary can be reloaded and used again in the same real-world environment in which it was defined. As shown in FIG. 9, a memory device, referred to as a memory device 900, may be included in HMD system 200. Memory device 900 may store a table or virtual boundary library that contains a plurality of physical definitions 902A-D. Each of physical definitions 902A-D may be associated with a virtual boundary 904A-D, respectively. In some embodiments, the virtual boundary library may further indicate whether an entry corresponds to a modification, for example to determine a history of modifications which may allow the user to undo/redo modifications. Method 100 may include operations of performing a real-world environment check that may include generating a provisional physical definition of the real-world environment and then comparing that definition with physical definitions 902A-D included in memory device 900. When a match is found as a result of the comparison, processing subsystem 210 may permit use of the corresponding virtual boundary by HMD system 200. Processing subsystem 210 may deny use of the virtual boundary by HMD system 200 when the real-world environment check does not result in finding a match and require the user to define a new virtual boundary.

According to the aspects described herein, a user of a VR system may modify a previously defined virtual boundary. Wearing an HMD device, the user may view the virtual boundary overlaid onto a pass-through view of the real-world environment. The user may use a hand-held controller to draw modifications to the virtual boundary. The HMD device and hand-held controller may allow the user to intuitively modify the virtual boundary by "drawing" or "paint-brushing" the modification. Allowing the user to modify the virtual boundary may prevent the user from having to redefine the virtual boundary completely from the beginning if a correction is needed. The user may also be visually and/or aurally notified if corrections are needed to the virtual boundary and may then correct the virtual boundary in real time. Thus, the user may be presented a more efficient and intuitive interface for defining and modifying the virtual boundary.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive sensor data to be transformed, transform the sensor data, output a result of the transformation to display a virtual boundary, use the result of the transformation to define and/or modify the virtual boundary, and store the result of the transformation to establish the virtual boundary. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A method comprising:
capturing image data associated with a view of a real-world environment using an imaging system of a head-mounted display system;
displaying a pass-through view of the real-world environment, based at least in part upon the image data, to a user in a display of the head-mounted display system;
receiving an indication of a reference elevation representing a plane of the real-world environment;
monitoring an orientation of a direction indicator to generate first orientation data and to establish, with respect to the reference elevation, a virtual boundary for a virtual-world environment;
displaying the virtual boundary in the pass-through view of the real-world environment;
determining whether a dimension of the virtual boundary satisfies a minimum threshold value;
displaying a notification when the dimension of the virtual boundary does not satisfy the minimum threshold value;
receiving a request from a user to modify the virtual boundary;
in response to the request from the user, monitoring the orientation of the direction indicator to generate second orientation data; and
modifying the virtual boundary based on the reference elevation and the second orientation data.

2. The method of claim 1, further comprising presenting an indication of the minimum threshold value to the user if the dimension does not satisfy the minimum threshold value.

3. The method of claim 1, wherein modifying the virtual boundary comprises resetting the virtual boundary based on the reference elevation and the second orientation data.

4. The method of claim 1, wherein the dimension comprises a length or a width of the virtual boundary.

5. The method of claim 1, wherein the dimension comprises an area of the virtual boundary.

6. The method of claim 1, further comprising displaying the virtual boundary in a first color if the dimension does not satisfy the minimum threshold value and displaying the virtual boundary in a second color if the dimension satisfies the minimum threshold value.

7. The method of claim 1, wherein the first and second orientation data includes elevation data of an elevation of the direction indicator with respect to the reference elevation.

8. The method of claim 7, wherein modifying the virtual boundary comprises determining an intersection between the plane and a virtual line that extends from the direction indicator at an elevation indicated by the elevation data and at the orientation indicated by the second orientation data.

9. The method of claim 1, wherein:
at least a portion of the captured image data has lens-induced distortion;
the displaying the pass-through view of the real-world environment comprises correcting the lens-induced distortion in the image data to produce a compensated view of the real-world environment; and
the displaying the virtual boundary comprises superimposing the virtual boundary on the compensated view of the real-world environment.

10. The method of claim 1, wherein modifying the virtual boundary includes adding portions to or subtracting portions from the virtual boundary.

11. The method of claim 1, further comprising receiving a confirmation of the reference elevation.

12. A tangible, non-transitory computer-readable storage medium having instructions stored thereon that, when executed by a processing system, cause the processing system to perform operations comprising:
capturing image data associated with a view of a real-world environment using an imaging system of a head-mounted display system;
displaying a pass-through view of the real-world environment, based at least in part upon the image data, to a user in a display of the head-mounted display system;
receiving an indication of a reference elevation representing a plane of the real-world environment;
monitoring an orientation of a direction indicator to generate first orientation data and to establish, with respect to the reference elevation, a virtual boundary for a virtual-world environment;
displaying the virtual boundary in the pass-through view of the real-world environment;
determining whether a dimension of the virtual boundary satisfies a minimum threshold value;
displaying a notification when the dimension of the virtual boundary does not satisfy the minimum threshold value;
receiving a request from a user to modify the virtual boundary;
in response to the request from the user, monitoring the orientation of the direction indicator to generate second orientation data; and
modifying the virtual boundary based on the reference elevation and the second orientation data.

13. The non-transitory computer-readable storage medium of claim 12, further comprising instructions for presenting the minimum threshold value to the user if the dimension does not satisfy the minimum threshold value.

14. The non-transitory computer-readable storage medium of claim 12, wherein modifying the virtual boundary comprises resetting the virtual boundary based on the reference elevation and the second orientation data.

15. The non-transitory computer-readable storage medium of claim 12, wherein the dimension comprises a length or a width of the virtual boundary.

16. The non-transitory computer-readable storage medium of claim 12, wherein the dimension comprises an area of the virtual boundary.

17. The non-transitory computer-readable storage medium of claim 12, further comprising instructions for displaying the virtual boundary in a first color if the dimension does not satisfy the minimum threshold value and displaying the virtual boundary in a second color if the dimension satisfies the minimum threshold value.

18. The non-transitory computer-readable storage medium of claim 12, wherein the first and second orientation data includes elevation data of an elevation of the direction indicator with respect to the reference elevation.

19. The non-transitory computer-readable storage medium of claim 18, wherein modifying the virtual boundary comprises determining an intersection between the plane and a virtual line that extends from the direction indicator at an elevation indicated by the elevation data and at the orientation indicated by the second orientation data.

20. The non-transitory computer-readable storage medium of claim 12, wherein:
the captured view of the real-world environment has lens-induced distortion;
the displaying the pass-through view of the real-world environment comprises correcting the lens-induced distortion in the captured view to produce a compensated view of the real-world environment; and the displaying the virtual boundary comprises superimposing the virtual boundary on the compensated view of the real-world environment.

21. The non-transitory computer-readable storage medium of claim 12, wherein modifying the virtual boundary includes adding portions to or subtracting portions from the virtual boundary.

22. The non-transitory computer-readable storage medium of claim 12, further comprising instructions for receiving a confirmation of the reference elevation.

23. A head-mounted display system comprising:
a display secured to a user attachment system;
an imaging system;
a direction indicator; and
a processing system configured to:
capture image data associated with a view of a real-world environment using the imaging system;
display a pass-through view of the real-world environment, based at least in part upon the image data, to a user in the display;
receive an indication of a reference elevation representing a plane of the real-world environment;
monitor an orientation of the direction indicator to generate first orientation data and to establish, with respect to the reference elevation, a virtual boundary for a virtual-world environment;
display the virtual boundary in the pass-through view of the real-world environment;
determine whether a dimension of the virtual boundary satisfies a minimum threshold value;
display a notification when the dimension of the virtual boundary does not satisfy the minimum threshold value;
receive a request from a user to modify the virtual boundary;
in response to the request from the user, monitor the orientation of the direction indicator to generate second orientation data; and
modify the virtual boundary based on the reference elevation and the second orientation data.

24. The head-mounted display system of claim 23, wherein the processing system is further configured to present the minimum threshold value to the user if the dimension does not satisfy the minimum threshold value.

25. The head-mounted display system of claim 23, wherein modifying the virtual boundary comprises resetting the virtual boundary based on the reference elevation and the second orientation data.

26. The head-mounted display system of claim 23, wherein the dimension comprises a length or a width of the virtual boundary.

27. The head-mounted display system of claim 23, wherein the dimension comprises an area of the virtual boundary.

28. The head-mounted display system of claim 23, wherein the processing system is further configured to display the virtual boundary in a first color if the dimension does not satisfy the minimum threshold value and display the virtual boundary in a second color if the dimension satisfies the minimum threshold value.

29. The head-mounted display system of claim 23, wherein the first and second orientation data includes elevation data of an elevation of the direction indicator with respect to the reference elevation.

30. The head-mounted display system of claim 29, wherein modifying the virtual boundary comprises determining an intersection between the plane and a virtual line that extends from the direction indicator at an elevation indicated by the elevation data and at the orientation indicated by the second orientation data.

31. The head-mounted display system of claim 23, wherein:
the captured view of the real-world environment has lens-induced distortion;
the displaying the pass-through view of the real-world environment comprises correcting the lens-induced distortion in the captured view to produce a compensated view of the real-world environment; and
the displaying the virtual boundary comprises superimposing the virtual boundary on the compensated view of the real-world environment.

32. The head-mounted display system of claim 23, wherein modifying the virtual boundary includes adding portions to or subtracting portions from the virtual boundary.

33. The head-mounted display system of claim 23, wherein the processing system is further configured to receive a confirmation of the reference elevation.

* * * * *